United States Patent
Wong

(10) Patent No.: US 11,918,284 B2
(45) Date of Patent: Mar. 5, 2024

(54) SYSTEMS AND METHODS RELATED TO FLEXIBLE ANTENNAS

(71) Applicant: INTUITIVE SURGICAL OPERATIONS, INC., Sunnyvale, CA (US)

(72) Inventor: Serena H. Wong, Los Altos, CA (US)

(73) Assignee: INTUITIVE SURIGICAL OPERATIONS, INC., Sunnyvale, CA (US)

( * ) Notice: Subject to any disclaimer, the term of this patent is extended or adjusted under 35 U.S.C. 154(b) by 274 days.

(21) Appl. No.: 17/040,578

(22) PCT Filed: Mar. 28, 2019

(86) PCT No.: PCT/US2019/024564
§ 371 (c)(1),
(2) Date: Sep. 23, 2020

(87) PCT Pub. No.: WO2019/191415
PCT Pub. Date: Oct. 3, 2019

(65) Prior Publication Data
US 2021/0068897 A1    Mar. 11, 2021

Related U.S. Application Data

(60) Provisional application No. 62/649,974, filed on Mar. 29, 2018.

(51) Int. Cl.
*A61B 18/18* (2006.01)
*H05B 6/72* (2006.01)
(Continued)

(52) U.S. Cl.
CPC ........... *A61B 18/1815* (2013.01); *H05B 6/72* (2013.01); *A61B 2017/00867* (2013.01);
(Continued)

(58) Field of Classification Search
CPC ...... A61B 18/1815; A61B 2017/00867; A61B 2017/00964; A61B 2018/00083;
(Continued)

(56) References Cited

U.S. PATENT DOCUMENTS

| 5,026,959 | A | 6/1991 | Ito et al. |
| 10,029,105 | B2 * | 7/2018 | Ameri ................. A61N 1/3758 |

(Continued)

FOREIGN PATENT DOCUMENTS

| CN | 101784750 A | 7/2010 |
| CN | 102625670 A | 8/2012 |

OTHER PUBLICATIONS

Extended European Search Report for Application No. EP19774704.1, dated Nov. 15, 2021, 7 pages.

(Continued)

*Primary Examiner* — Michael F Peffley
*Assistant Examiner* — Amanda L Zink
(74) *Attorney, Agent, or Firm* — Haynes & Boone, LLP

(57) ABSTRACT

A flexible instrument comprises an antenna having a distal tip portion shaped to perforate tissue, a proximal base, and an antenna body therebetween. The antenna body comprises a patterned cylindrical structure having antenna body elements spatially separated from each other and having a proximal end coupled to the proximal base and a distal end coupled to the distal tip portion. The distal tip portion is disposed distally of the distal end. The antenna comprises a first material having a flexible plastic deformation limit and a second material plated onto the first material. The second material is more conductive than the first material. The flexible instrument further comprises an adjustment device configured to adjust pitch lengths between adjacent antenna body elements and is configured to generate a radiation (Continued)

pattern from the antenna that varies based on the pitch length between the adjacent antenna body elements to ablate tissue.

19 Claims, 18 Drawing Sheets

(51) Int. Cl.
*A61B 17/00* (2006.01)
*A61B 18/00* (2006.01)

(52) U.S. Cl.
CPC .............. *A61B 2017/00964* (2013.01); *A61B 2018/00083* (2013.01); *A61B 2018/00577* (2013.01); *A61B 2018/1823* (2013.01); *A61B 2018/1838* (2013.01); *A61B 2018/1846* (2013.01); *A61B 2018/1853* (2013.01); *A61B 2018/1861* (2013.01); *A61B 2018/1869* (2013.01); *A61B 2018/1892* (2013.01)

(58) Field of Classification Search
CPC .. A61B 2018/00577; A61B 2018/1823; A61B 2018/1838; A61B 2018/1846; A61B 2018/1853; A61B 2018/1861; A61B 2018/1869; A61B 2018/1892; H05B 6/72
See application file for complete search history.

(56) References Cited

U.S. PATENT DOCUMENTS

| | | | |
|---|---|---|---|
| 2002/0087151 A1* | 7/2002 | Mody | A61B 18/1492 606/41 |
| 2002/0193783 A1* | 12/2002 | Gauthier | A61B 18/18 606/17 |
| 2003/0028095 A1 | 2/2003 | Tulley et al. | |
| 2003/0083654 A1* | 5/2003 | Chin | A61B 18/1492 606/41 |
| 2003/0088242 A1* | 5/2003 | Prakash | A61B 18/18 606/33 |
| 2005/0010095 A1 | 1/2005 | Stewart et al. | |
| 2006/0206107 A1 | 9/2006 | Berube | |
| 2006/0259024 A1* | 11/2006 | Turovskiy | A61B 18/18 607/156 |
| 2008/0266203 A1 | 10/2008 | Rossetto et al. | |
| 2008/0287939 A1* | 11/2008 | Appling | A61B 18/24 606/15 |
| 2009/0326620 A1* | 12/2009 | Rossetto | A61B 18/18 607/101 |
| 2011/0009858 A1* | 1/2011 | Ormsby | A61B 18/1492 606/33 |
| 2011/0213351 A1* | 9/2011 | Lee | A61B 18/1815 606/41 |
| 2011/0282336 A1 | 11/2011 | Brannan et al. | |
| 2013/0267940 A1* | 10/2013 | Chiang | A61B 18/1815 606/33 |
| 2014/0114302 A1 | 4/2014 | Lee et al. | |
| 2014/0276743 A1 | 9/2014 | Curley | |
| 2014/0358140 A1 | 12/2014 | Emmons et al. | |
| 2015/0150627 A1 | 6/2015 | Brannan et al. | |
| 2015/0250540 A1 | 9/2015 | Behdad et al. | |
| 2015/0313670 A1 | 11/2015 | Shroff et al. | |
| 2015/0322759 A1* | 11/2015 | Okoniewski | E21B 43/2401 166/60 |
| 2017/0270401 A1 | 9/2017 | Kato | |
| 2018/0078309 A1 | 3/2018 | Van Der Weide et al. | |
| 2018/0266203 A1 | 9/2018 | Murphy | |

OTHER PUBLICATIONS

International Preliminary Report on Patentability for Application No. PCT/US2019/024564, dated Sep. 29, 2020, 8 pages.
International Search Report and Written Opinion for Application No. PCT/US2019/024564, dated Aug. 16, 2019, 15 pages.
Mohtashami Y., et al., "A Balun-Free Hybrid Helix/Monopole Antenna for Microwave Ablation," Department of Electrical and Computer Engineering, University of Wisconsin-Madison, Jan. 2018, 19 pages.
Pchelnikov Y.N., "Ring-Double-Bar Slow Wave Structure for High Power TWTs," IEEE Transactions on Electron Devices, Nov. 2016, vol. 63 (11), pp. 4479-4483.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

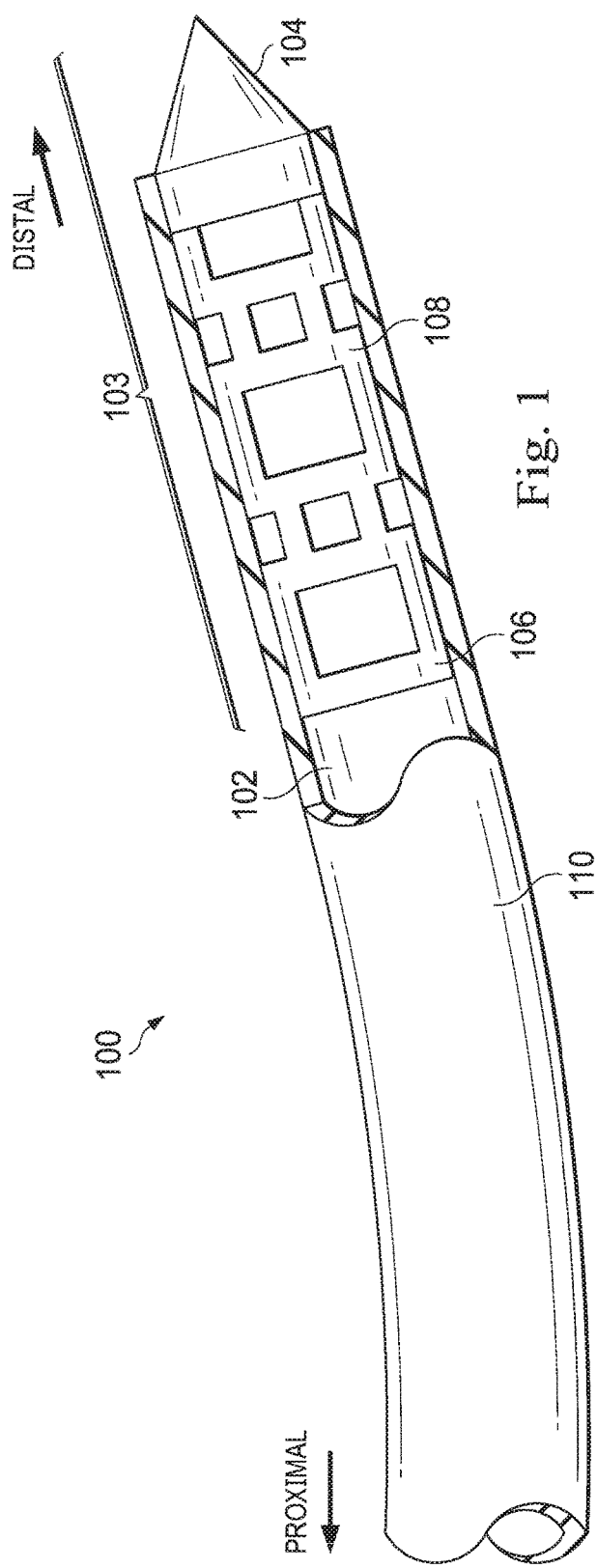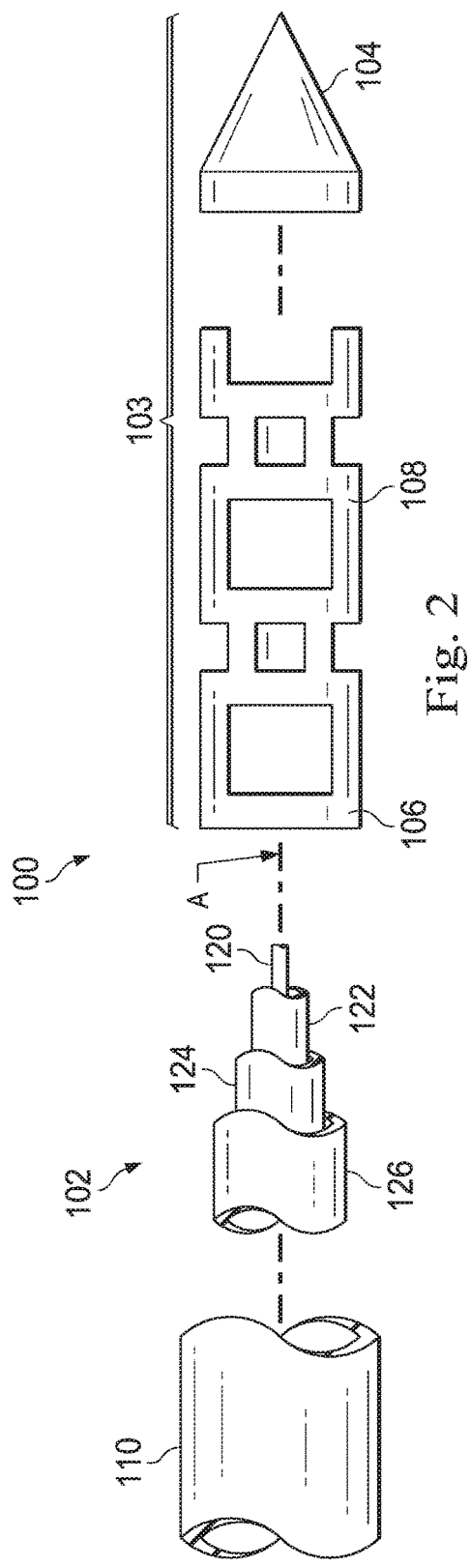

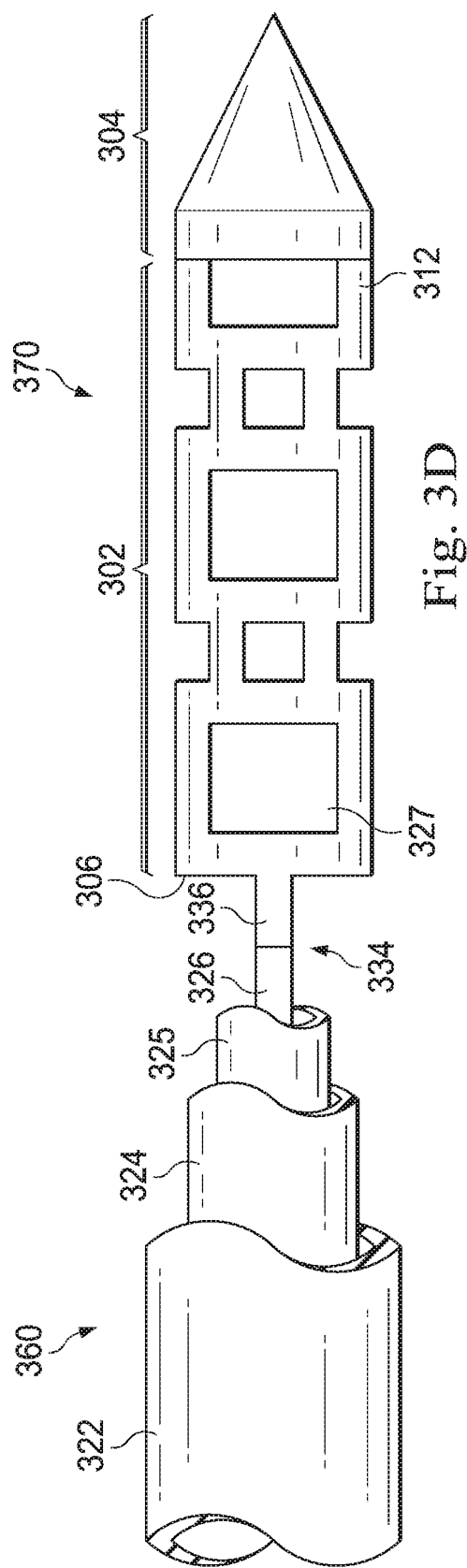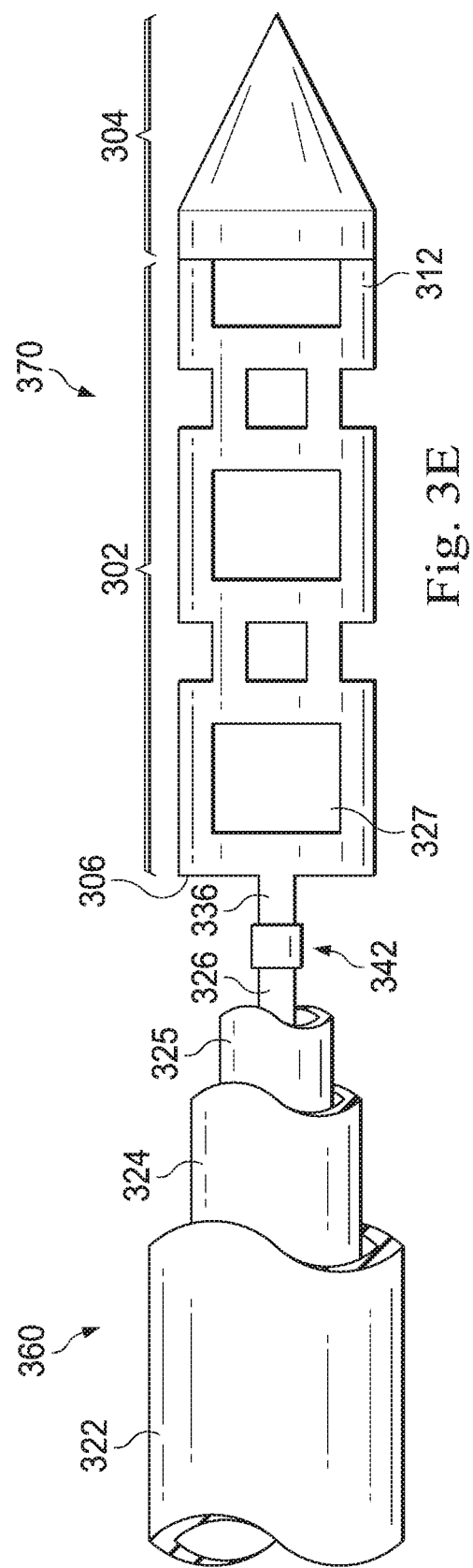

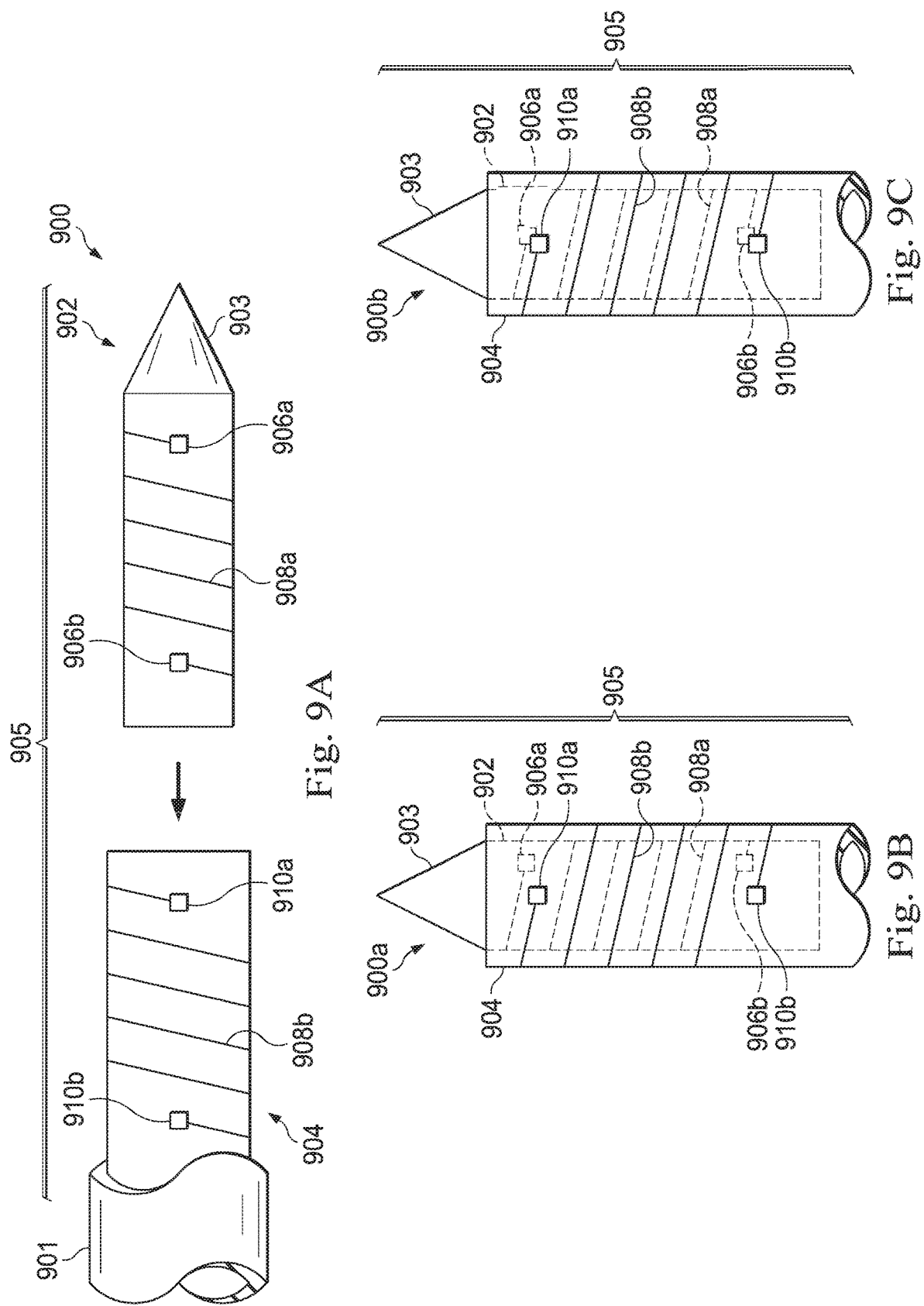

SYSTEMS AND METHODS RELATED TO FLEXIBLE ANTENNAS

CROSS-REFERENCE TO RELATED APPLICATIONS

This application is a U.S. national phase of International Application No. PCT/US2019/024564, filed Mar. 28, 2019 (and published as WO2019/191415), which designates the U.S. and claims priority to and the benefit of U.S. Provisional Application 62/649,974, filed Mar. 29, 2018, both of which are incorporated by reference herein in their entirety.

FIELD

The present disclosure is directed to systems and methods for improving tissue ablation with novel antenna configurations in a minimally invasive manner from a steerable elongate device.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions an operator may insert minimally invasive medical instruments (including surgical, diagnostic, therapeutic, or biopsy instruments) to reach a target tissue location. One such minimally invasive technique is to use a flexible and/or steerable elongate device, such as a flexible catheter, that can be inserted into anatomic passageways and navigated toward a region of interest within the patient anatomy.

Tissue ablation devices currently have few options for small form factors while preserving flexibility to navigate tortuous anatomy. It would be advantageous to provide materials and designs that support flexible navigation of antennas for tissue ablation that retain antenna shape, improve manufacturability, and/or facilitate control of tissue ablation parameters, and that are suitable for use during minimally invasive medical techniques.

SUMMARY

The embodiments of the invention are best summarized by the claims that follow the description.

Consistent with some embodiments, systems and methods of the present disclosure include an ablation assembly, including a patterned cylindrical structure comprising a proximal end and a distal end, the proximal end being coupled to a conducting cable. The patterned cylindrical structure further comprises a first material having a flexible plastic deformation limit such that a strain as the patterned cylindrical structure bends through a curve remains below the flexible plastic deformation limit. Further, the patterned cylindrical structure comprises a second material plated onto the first material, the second material being more conductive than the first material and being electrically coupled to the conducting cable to generate a radiation pattern to ablate tissue.

Consistent with some embodiments, a flexible instrument comprises an antenna having a distal tip portion, a proximal base, and an antenna body therebetween. The antenna body comprises a patterned cylindrical structure having a proximal end coupled to the proximal base and a distal end coupled to the distal tip portion. The flexible instrument is configured to generate a radiation pattern from the antenna to ablate tissue.

Consistent with some embodiments, a method comprises identifying a desired ablation zone for a target tissue. The desired ablation zone has at least one ablation zone parameter. The method further comprises determining physical parameters of a flexible instrument for generating an ablation energy to create the desired ablation zone size for the target tissue. The flexible instrument includes an antenna having a distal tip portion, a proximal base, and an antenna body therebetween. The antenna body comprises a patterned cylindrical structure having a proximal end coupled to the proximal base and a distal end coupled to the distal tip portion. The method also comprises determining at least one ablation parameter of the flexible instrument for generating the ablation energy to create the desired ablation zone for the target tissue.

Consistent with some embodiments, A method comprises identifying a desired ablation zone for a target tissue and adjusting physical parameters of a flexible instrument for generating an ablation energy to create the desired ablation zone for the target tissue. The flexible instrument includes an antenna having a distal tip portion, a proximal base, and an antenna body therebetween. The antenna body comprises a patterned cylindrical structure having a proximal end coupled to the proximal base and a distal end coupled to the distal tip portion. The method also comprises delivering the ablation energy to create the desired ablation zone size for the target tissue.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 1 is a simplified diagram of a flexible antenna system according to some embodiments.

FIG. 2 is a simplified exploded diagram of a flexible antenna system according to some embodiments.

FIG. 3D is a simplified diagram of a flexible antenna system according to some embodiments.

FIG. 3E is a simplified diagram of a flexible antenna system according to some embodiments.

FIG. 9A is a simplified diagram of a flexible and adjustable antenna system according to some embodiments.

FIG. 9B is a simplified diagram of a flexible and adjustable antenna system in a first configuration according to some embodiments.

FIG. 9C is a simplified diagram of a flexible and adjustable antenna system in a second configuration according to some embodiments.

Figure 3A:
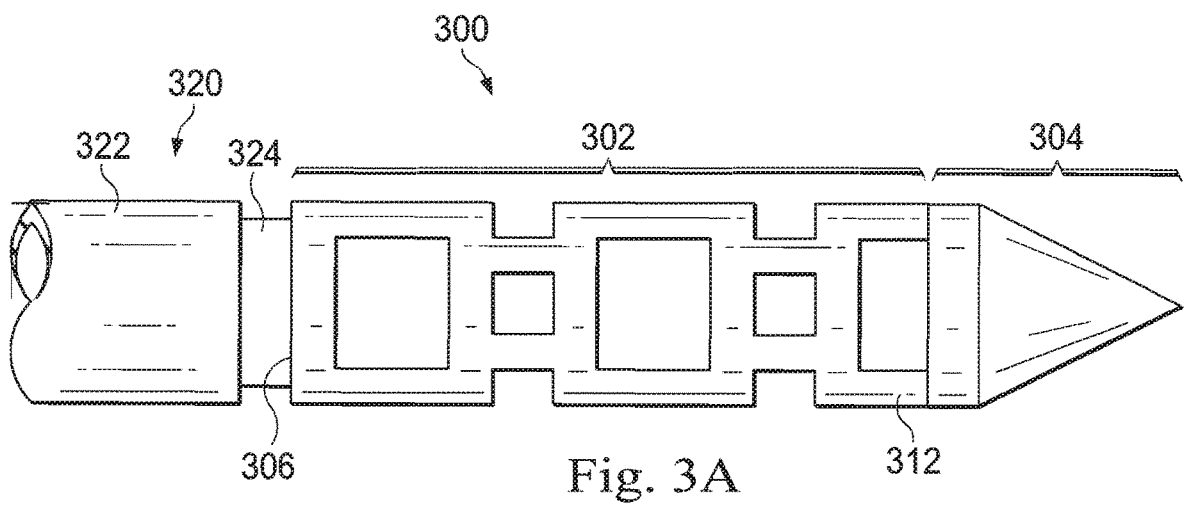
FIG. 3A is a simplified diagram of a flexible antenna according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, as would be appreciated by one skilled in the art, embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment may be used or omitted as applicable from other illustrative embodiments. For the sake of brevity, the numerous iterations of these combinations will not be described separately. For simplicity, in some instances the same reference numbers are used throughout the drawings to refer to the same or like parts.

Minimally invasive techniques may include the use of tissue ablation devices. Tissue ablation may be accomplished by electrical energy from frequencies ranging from very low frequency up to microwave and higher. However, for applications that rely upon an antenna to emit these frequencies into surrounding tissue, (i.e., accomplishing ablation by dielectric heating), difficulties may arise. For example, microwave antennas may be formed from coaxial cables comprising a conducting material (e.g., copper) that is relatively inflexible, particularly in the small sizes used for endoluminal applications. The rigidity of the conducting material may limit the utility of the antenna in anatomical regions that require traversal of one or more luminal bends to reach a region of interest. Though the antenna may bend at a curve in the lumen, the rigidity of the material may prevent the antenna from recovering from the bend when positioned at the target tissue to begin ablation. In other words, the antenna may be unable to re-straighten to its pre-bend form prior to performing the ablation on the target tissue. Additionally, most antennas are monopoles or dipoles where the length of the antenna is set by the frequency. It may be difficult to control the size of an ablation zone and minimum insertion depth of these antennas for tissue ablation, since the length of the antenna, and therefore the length of insertion (and ablation size) is dictated by the frequency of operation selected at manufacture for the antenna.

Additionally, the length and configuration of the wire can affect the axial stiffness and ease of puncture. With reference to FIG. 1, a simplified diagram of a flexible antenna system 100, according to some embodiments, is illustrated. The flexible antenna system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 1, the flexible antenna system 100 includes an antenna assembly 103 at a distal end of the antenna system 100 and a cable 102 (sometimes referred to as a conducting cable assembly) that extends between a proximal end of the antenna system 100 and the antenna assembly 103. In some embodiments, the antenna assembly 103 is formed separately from the cable 102 and is coupled to a portion of the cable 102. The cable 102 may assume a variety of configurations capable of conducting electricity/ electrical signals. The antenna assembly 103 includes an antenna tip portion 104 coupled to a distal end of an antenna body 108. An antenna base 106 of the antenna assembly 103 is coupled to or integrally formed with the cable 102. The antenna body 108 may be formed with one or more of a variety of generally cylindrical or tubular patterns including bar and ring patterns, cutout patterns, slotted patterns, and helical patterns, as will be described in detail below. A sheath 110 surrounds the cable 102 and, in some embodiments, surrounds portions of the antenna assembly 103. The sheath may be formed, for example, from a plastic material, elastomeric, or otherwise flexible material.

FIG. 2 illustrates the flexible antenna system 100 exploded along a longitudinal axis A. In some embodiments the cable 102 may be a coaxial cable including an inner conductor 120 surrounded by a dielectric insulator layer 122. An outer conductor 124 surrounds the dielectric insulator layer 122. A protective plastic jacket 126 surrounds the outer conductor 124. The inner conductor 120, the dielectric insulator 122, the outer conductor 124, and the jacket 126 may all be coaxial with the axis A. Other coaxial cable configurations with different configurations, shapes, etc. of inner conductor, dielectric, and outer conductor could also be used.

FIGS. 3A-3E illustrate various embodiments for coupling the cable 102 to the antenna assembly 103. FIG. 3A illustrates an antenna assembly 300 according to some embodiments. The antenna assembly 300 may be substantially similar to the antenna assembly 103, with differences as described. The antenna assembly 300 includes antenna body 302 coupled to or integrally formed with an antenna tip portion 304. The antenna body 302 includes an antenna base 306 and antenna body distal end 312. The antenna assembly 300 is coupled to a cable 320 which may be substantially similar to cable 102. The cable 320 includes a jacket 322 and an outer conductor 324. In the embodiment of FIG. 3A, the antenna assembly 300 is coupled to and in electrical connection with the cable 320 via outer conductor 324. The coupling between the antenna body 302 and the outer conductor 324 may be achieved by crimping, welding, soldering, or other connections that produce electrical connection. Alternatively, the outer conductor 324 may be form fitted within the antenna base 306, where the antenna base 306 is placed around a distal end of the outer conductor 324. In another embodiment, the antenna body can be cut directly from the coaxial cable. In such embodiments, the inner conductor of the cable may be left unconnected to the antenna body 302 or could connect at the antenna tip portion 304.

Figure 3B:
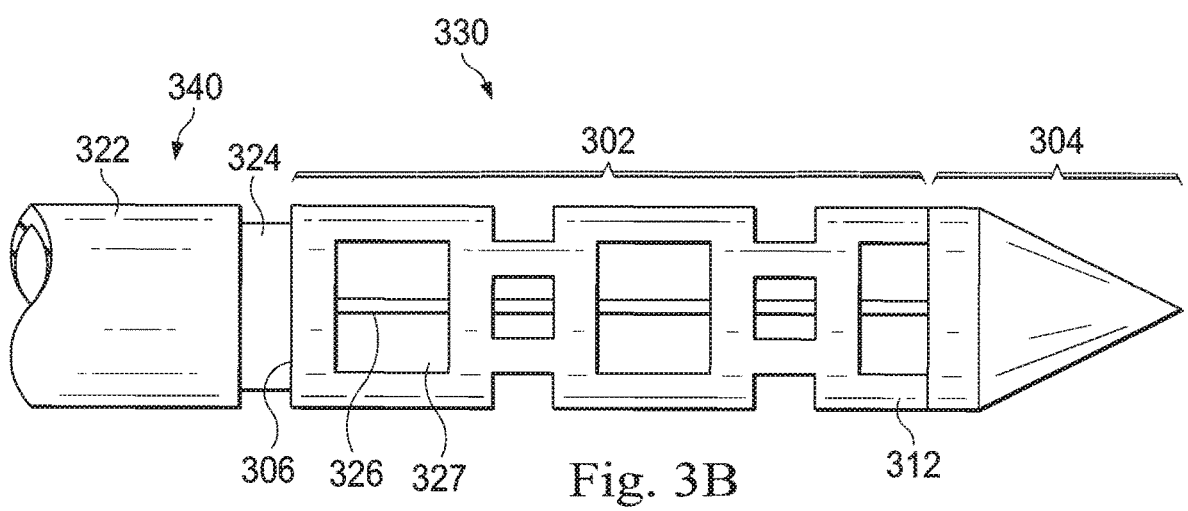
FIG. 3B is a simplified diagram of a flexible antenna system according to some embodiments.

FIG. 3B illustrates an antenna assembly 330 according to some embodiments. The antenna assembly 330 may be substantially similar to the antenna assembly 103, 300 with differences as described. The antenna assembly 330 includes the antenna body 302, the antenna tip portion 304, the antenna base 306 and antenna body distal end 312 as previously described. The antenna assembly 330 is coupled to a cable 340 which may be substantially similar to cable 102, 320. The cable 340 includes the jacket 322, the outer conductor 324, and an inner conductor 326. In the embodiment of FIG. 3B, the distal section of the antenna assembly 330 is coupled to and in electrical connection with the cable 340 via inner conductor 326. The coupling between the antenna body 302 and the inner conductor 326 may be achieved by crimping, welding, soldering, or other connections that produce electrical connection. The inner conductor 326 extends through a central lumen 327 of the antenna body 302 and connects to a distal end of the antenna assembly 330 such as at the antenna tip portion 304. The inner conductor 326, in this configuration, may provide axial strength to the antenna assembly 350.

Figure 3C:
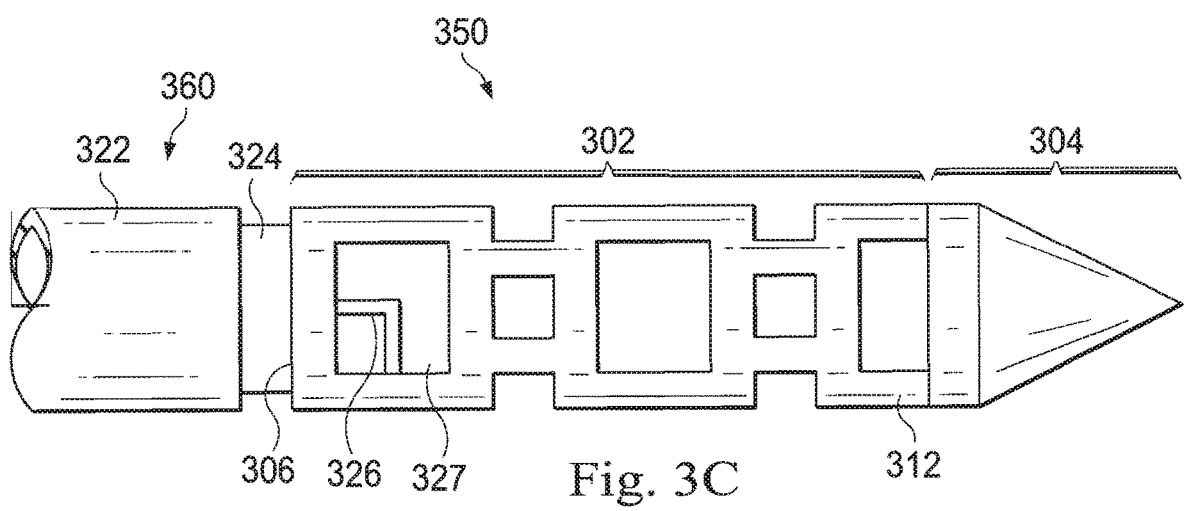
FIG. 3C is a simplified diagram of a flexible antenna system according to some embodiments.

FIG. 3C illustrates an antenna assembly 350 and a cable 360 according to some embodiments. The antenna assembly 350 is substantially similar to the antenna assembly 330, and the cable 360 is substantially similar to cable 340. The cable 360 includes the jacket 322, the outer conductor 324, and an inner conductor 326. In this embodiment, the inner conductor 326 may extend partially through the central lumen 327 of the antenna body 302 and may attach to an inner surface of the antenna body 302. The coupling between the antenna body 302 and the inner conductor 326 may be achieved by crimping, welding, soldering, or other connections that produce electrical connection. In this embodiment the inner conductor 326 is connected to the antenna body 302 near the antenna base 306. As shown in this embodiment, the inner conductor 326 may be bent at approximately 90 degrees to connect with the antenna assembly 350. Alternatively, the inner conductor may be unbent. The inner conductor 326, in this configuration, may provide axial strength to the antenna assembly 350 if it is connected towards the distal end of the antenna body. In other embodiments, the inner conductor 326 may connect anywhere along the length of the antenna body 302. The outer conductor 324 may be left unconnected to the antenna assembly 350 or may be coupled to the antenna assembly 350 as described with respect to FIG. 3A. In the case where the outer conductor is not electrically connected to the antenna body, an insulating body may be needed to provide mechanical coupling but not electrical coupling.

FIG. 3D illustrates an antenna assembly 370 according to some embodiments. The antenna assembly 370 may be substantially similar to the antenna assembly 350 with any differences as described. In this embodiment, a coupling strut 336 extends proximally from the antenna base 306. The antenna assembly 330 is coupled to the cable 360 which may be substantially similar to cable 340. The cable 340 includes the jacket 322, the outer conductor 324, a dielectric insulator layer 325, and an inner conductor 326. In this embodiment, the coupling strut 336, is electrically connected to the inner conductor 326 by a weld joint 334 (or, alternatively, solder, adhesive, or a combination of solder, adhesive, and/or weld such as laser weld). The weld joint 334 is illustrated as a butt joint, although other types of joints may be applicable.

FIG. 3E illustrates the antenna assembly 370 according to some embodiments. In this embodiment, the coupling strut 336 is coupled to the inner conductor 326 by sleeve 342. The sleeve 342 may be electrically conductive (i.e., formed from an electrically conductive material) so that the inner conductor 326 is spaced apart from the coupling strut 336. In some embodiments the inner conductor 326 and the antenna base 306 are in physical contact with each other and encased within the sleeve 342. If the inner conductor 326 and the coupling strut 336 remaining in physical contact to each other, the sleeve 342 may be electrically non-conductive. Although the above FIGS. 3D-3E have illustrated the antenna base 306 connected to the inner conductor 326, the same coupling mechanisms (e.g., a weld joint or a sleeve) may, alternatively, be applied to connect the antenna base 306 to the outer conductor 324 instead.

Figure 4A:
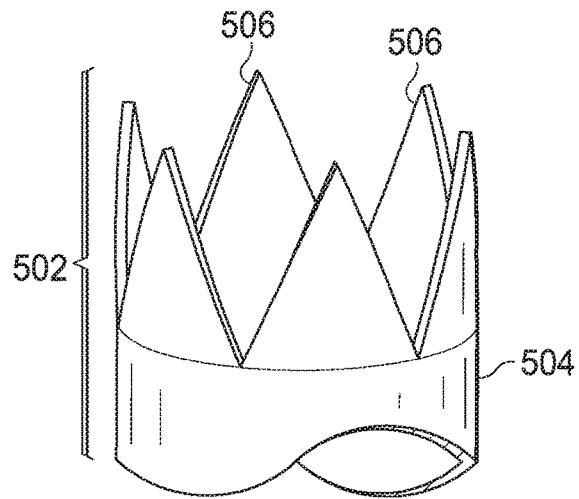
FIGS. 4A and 4B are side views of a simplified diagram of a flexible antenna tip according to some embodiments.
Figure 4B:
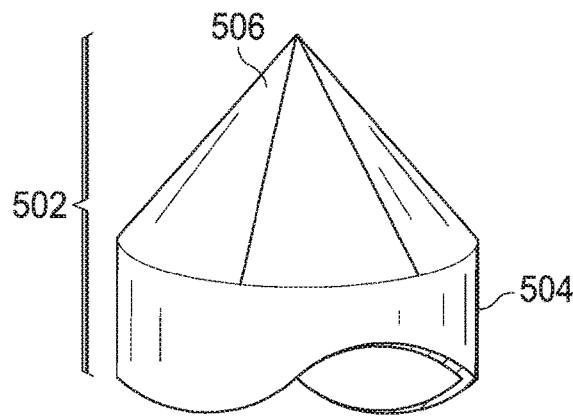

FIGS. 4A-4E illustrate various embodiments of antenna tip portions that may be used as the antenna tip portion 104, 304. In some embodiments, the antenna tip portion is formed from the same material as the antenna body 108, 302. In other embodiments, the antenna tip portion may be formed separately and attached to the antenna body 108, 302. FIG. 4A illustrates a side view of an antenna tip portion 502 according to some embodiments. The antenna tip portion 502 includes a base portion 504 and multiple tabs or tip sections 506. The antenna tip portion 502 includes six tip sections 506, but alternative embodiments may include more or fewer tip sections. In various embodiments, the antenna tip portion may be integral with the antenna body. For example, the antenna tip portion may be formed from a distal end section of the antenna body by cutting away areas of the antenna body to form the tip sections. FIG. 4B illustrates a side view of the antenna tip portion 502 with the tip sections 506 drawn together. The tip sections 506 may be crimped or collapsed so that the distal portion of each tip section 506 is substantially in contact with the distal portion of the other tip sections 506 to form a cone. In some embodiments, the tip sections 506 may be further held in the cone shape such as by an adhesive, a weld (e.g., laser weld), solder, or other mechanism to preserve the cone shape and configuration. The resulting antenna tip portion 502 may be used, for example, in puncturing or separating tissue. The antenna tip portion 502 may be used with any of the antenna bodies previously described. In various alternatives, the antenna tip portion may be blunt rather than pointed, with rounded or square tips for example, to traverse tissue when sent with a needle. The tip portion could also be made entirely out of the same material or out of two materials. In one example, the very distal tip is formed from stainless steel or another type of material that may be sharpened to enable easy puncture through tissue. The distal end of the tip may be made from plastic to isolate it from the antenna body. The different materials can be glued, over molded, welded, threaded and screwed, etc. or joined by any other means.

The use of tabbed sections for crimping may also or alternatively be applied at the antenna bases 106, 306 or strut 336. In these embodiments, the tabbed sections may be crimped until the tabbed sections engage in contact with a portion of the cable, such as the inner or outer conductor. For example in the embodiment of FIG. 3A, tabbed sections at the antenna proximal end 306 may be crimped against the outer conductor 324 to form an electrical connection between at least some of the crimped, tab sections and the conductor 324. The coupling may further be secured in place by, for example, weld points, solder, adhesive, or another type of securing technique.

Figure 4C:
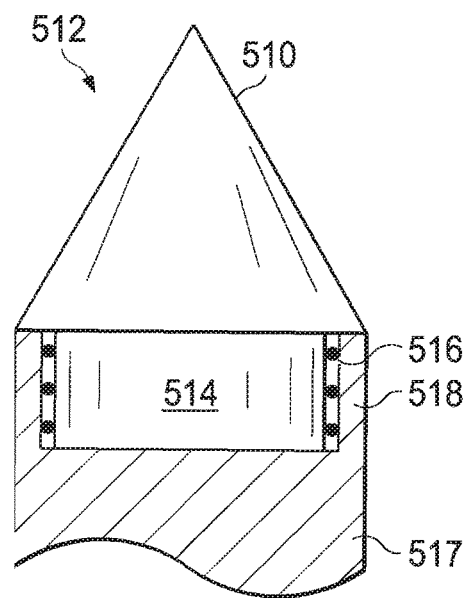
FIG. 4C is a side view of a simplified diagram of a flexible antenna tip according to some embodiments.

FIG. 4C illustrates a side cross-sectional view of an antenna tip portion 512 according to some embodiments. The antenna tip portion 512 includes a conical section 510 and an insert section 514. The insert section 514 may be set within a distal end 517 of an antenna body (e.g., antenna body 108, 302). The insert section 514 engages with inner surfaces 518 of the receiving distal end 517. According to some embodiments, the insert section 514 is secured to select portions of the inner surfaces of the receiving distal end 517 at weld points 516 (e.g., one or more weld points around a perimeter of the insert section 514). The weld points 516 may alternatively be points of solder or adhesion using some other material/securing approach. In some embodiments, the antenna body may be sandwiched between an insert and a portion of the tip that goes concentrically around the outside diameter of the antenna body. Upon application of heat, these two sections will melt together to form a good bond. Holes in the antenna body may need to be formed in order to allow the material to flow through.

Figure 4D:
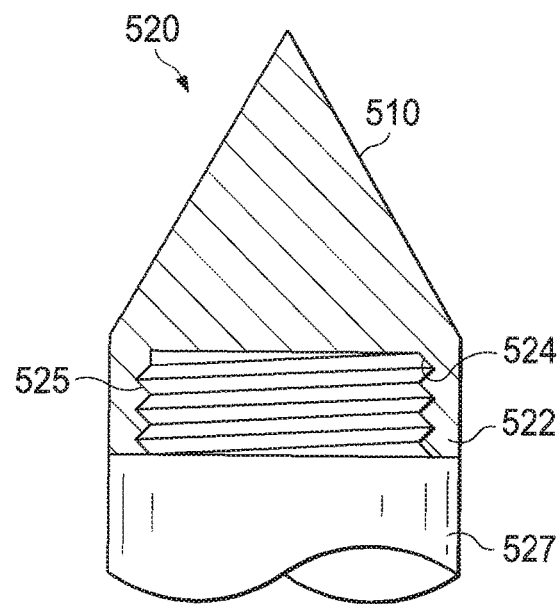
FIG. 4D is a side view of a simplified diagram of a flexible antenna tip according to some embodiments.

FIG. 4D illustrates a side cross-sectional view of an antenna tip portion 520 according to some embodiments. The antenna tip portion 520 includes the conical section 510 and a coupling section 522. The coupling section 522 includes inner threads 524, around an interior perimeter of the antenna tip portion 520, secured to a threaded distal end 527 of an antenna body (e.g., antenna body 108, 302). The distal end 527 of the antenna body includes outer threads 525 around a perimeter of the distal end. The antenna tip portion 520 may be secured to the antenna body by threading the inner threads 524 onto the outer threads 525. The threaded connection may provide a secure lock between the antenna tip portion and the antenna body. Additionally, the coupling may be further secured by welding, soldering, or cementing with adhesive/etc. The structure can be additionally heated to further melt the plastic and enhance the bond.

Figure 4E:
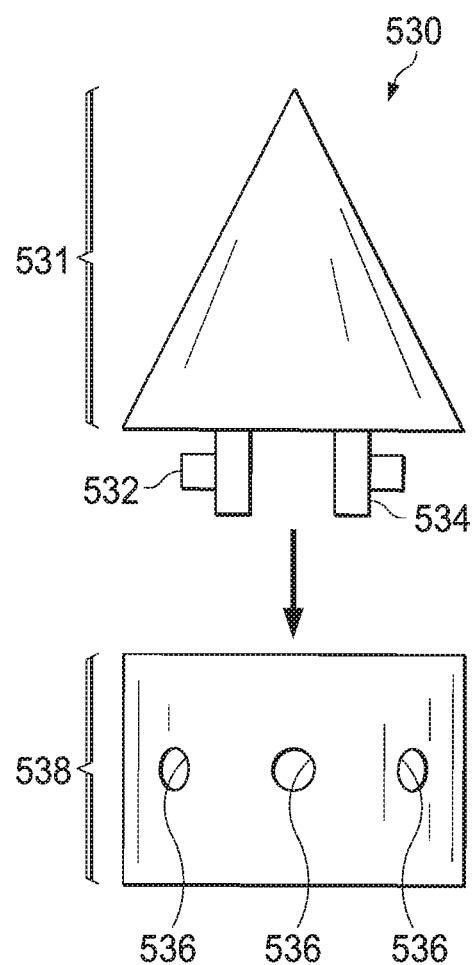
FIG. 4E is a side view of a simplified diagram of a flexible antenna tip according to some embodiments.

FIG. 4E illustrates an antenna tip portion 530 with a conical section 531 insertable into a receiving distal end 538 of an antenna body. The conical section 531 includes tabs 532 attached to an insert 534. The insert 534 includes two distinct bars extending from a proximal end of the conical section 531 toward the receiving distal end 538 of the antenna body. Alternatively, the insert 534 may be a single block extending from the conical section 531 (e.g., a round "peg") that has one or more tabs 532 at various points around the insert 534's circumference (e.g., equidistant points, etc.).

The receiving distal end 538 of the antenna body includes one or more receiving slots 536 that have a shape corresponding to that of the tabs 532. For example, if the tabs 532 are each round, the corresponding receiving slots 536 are round, with a radius just larger than that of a tab 532 to allow the tabs 532 to enter the receiving slots 536 and remain there. Although described as being round, the receiving slots 536 (and the corresponding tabs 532) may assume a variety of shapes, so long as the shapes correspond to each other (e.g., round tabs to round slots, square tabs to square holes, etc.).

In use, the insert 534 is inserted into the receiving distal end 538 until the tabs 532 releasably engage with corresponding receiving slots 536. This is facilitated by the insert 534 having a size (e.g., radius) that is just smaller than the radius of the corresponding receiving distal end 538, such that the tabs 532's heights may cause them to "snap" into place once they reach corresponding receiving slots 536. After releasably engaging with corresponding receiving slots 536, they may be further secured into place by adhesive or some other mechanism like heating and melting plastic, or otherwise left secured merely by the friction force between tabs 532 and walls of corresponding receiving slots 536.

Figure 5A:
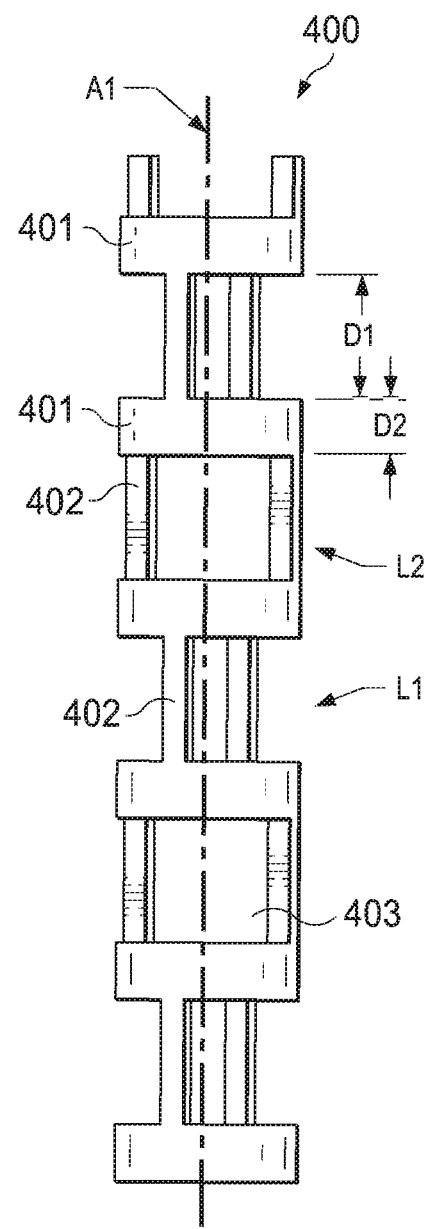
FIG. 5A is a simplified diagram of a flexible antenna system according to some embodiments.
Figure 5B:
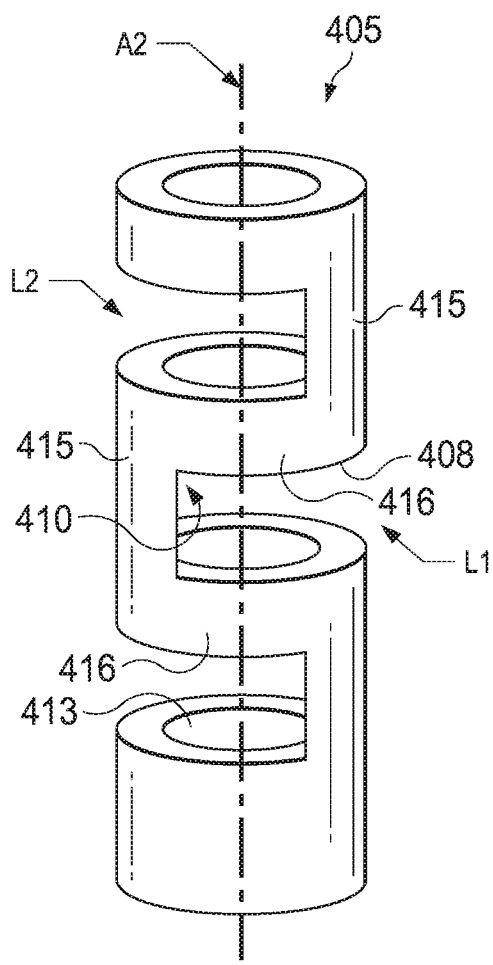
FIG. 5B is a simplified diagram of a flexible antenna system according to some embodiments.
Figure 5C:
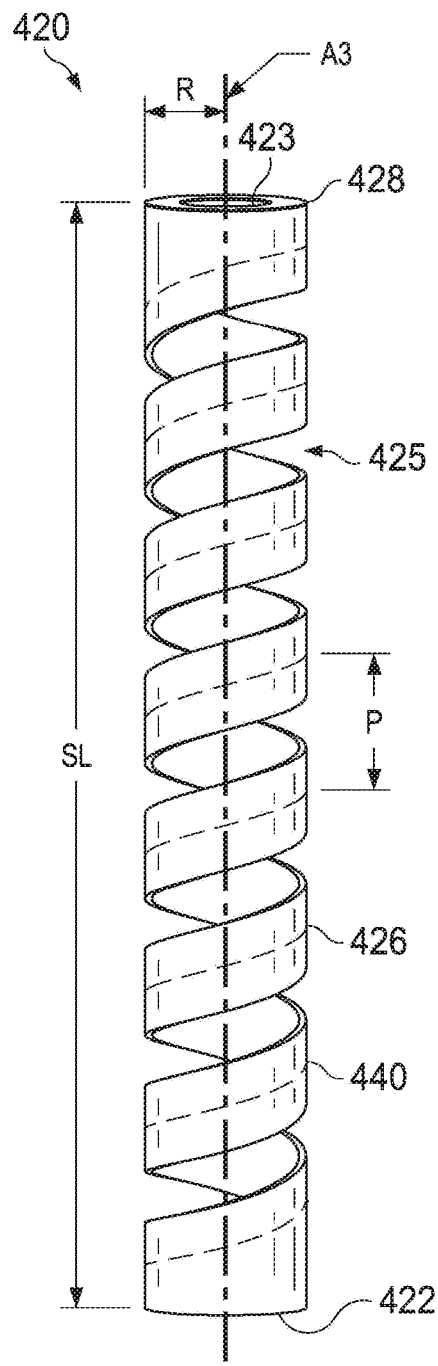
FIG. 5C is a simplified diagram of a flexible antenna system according to some embodiments.

FIGS. 5A-5C illustrate various embodiments of cylindrical patterned antenna bodies that may be used as the antenna body 108, 302. The antenna bodies are radiating structures that generate radiation patterns as shown, for example, in FIG. 7. In the absence of shielding around the antenna body or other obstruction to the radiation pattern, the radiation pattern transverse to the longitudinal axis of the antenna may extend further than the radiation pattern distal of the antenna tip. The antenna bodies may be formed from steel or another suitable electrically conductive material or may be coated with a conductive material. FIG. 5A illustrates a double bar ring antenna body 400 according to some embodiments. The antenna body 400 is generally cylindrical and axially aligned along an axis A1. A central lumen 403 extends longitudinally through the antenna body 400. The antenna body 400 may be fabricated by cutting portions from a tube to form longitudinal bars 402 and radial rings 401. In this embodiment, the rings 401 are arranged about and along the axis A1. Each ring 401 is spaced apart from another ring 401 by a pair of bars 402 arranged in parallel on opposite sides of the axis A1. The paired bars 402 at a level L1 may be rotated approximately 90 degrees relative to the paired bars 402 at an adjacent level L2. A variety of configurations of the paired bar antenna body may be suitable. For example, the paired bars may have a length D1 that is longer, shorter, or the same as the height D2 of the ring. The antenna body may further include additional cut-outs, rounded corners, or variations between the structure at adjacent levels to achieve desired flexibility, antenna performance, or ease of manufacture.

FIG. 5B illustrates a single bar ring antenna body 405 according to some embodiments. The antenna body 405 is generally cylindrical and axially aligned along an axis A2. A central lumen 413 extends longitudinally through the antenna body 405. The antenna body 405 may be fabricated by cutting slots into a tube to form longitudinal bars 415 and radial rings 416. In this embodiment, the rings 416 are arranged about and along the axis A2. Each ring 416 is spaced apart from another ring 401 by a single bar 415. The bar 415 at a level L1 may be rotated approximately 180 degrees relative to the bar 415 at an adjacent level L2. Each ring 416 defines a ring edge 408, and each bar 415 defines a bar edge 410. The angle of the intersecting edges 408, 410 may be selected to reduce stress under bend conditions. For example, each angle may be approximately 90 degrees as shown in FIG. 5B. In other embodiments the angle may be larger or smaller or the angles may be different at different levels. In some embodiments, the edges 408, 410 are rounded instead of square so as to further reduce stress under bend conditions, therefore added to the resiliency of the materials of the patterned cylindrical structure. Sections of the tubing can also be thinned or shaped in certain ways to allow material spaces to move and enhance flexibility.

FIG. 5C illustrates a helical antenna body 420 according to some embodiments. The antenna body 420 is generally cylindrical and axially aligned along an axis A3. A central lumen 423 extends longitudinally through the antenna body 420. The antenna body 420 may have end surfaces 422, 428 be fabricated by cutting a helical slot 425 into a tube to form a helical coiled ribbon structure 426. In some embodiments, the helical ribbon structure 426 is formed by laser cutting a tube. Alternatively, instead of being laser cut, the helical ribbon structure may be formed by injection molding.

Figure 5D:
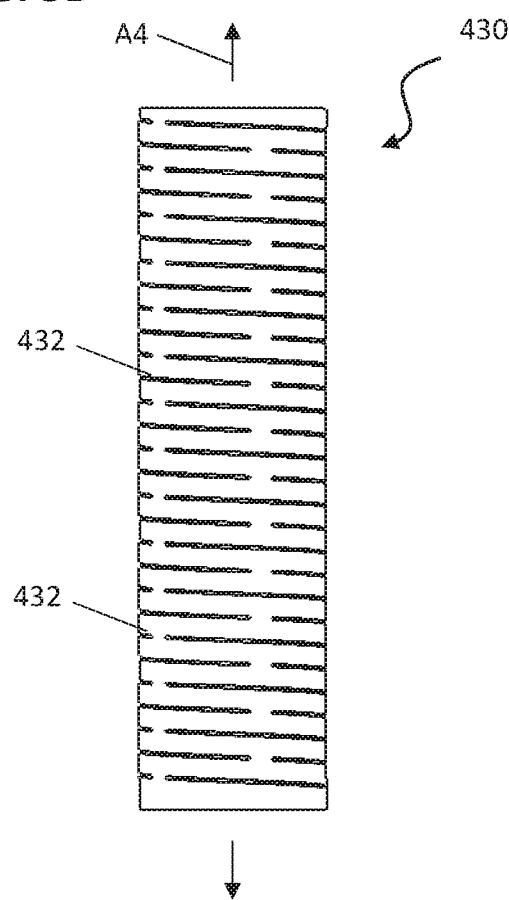
FIG. 5D is a simplified diagram of a flexible antenna system according to some embodiments.

FIG. 5D illustrates a slotted antenna body 430 according to some embodiments. The antenna body 430 is generally cylindrical and axially aligned along an axis A4. The antenna body 430 may include spiral slots 432 that extend less than 360 degrees around the body. In alternative embodiments, the antenna body may be formed from a tube with symmetrical or non-symmetrical cuts, including a non-symmetrical pattern of slots.

The ring bar structure may be advantageous over other structures because of the compromise between bending and axial stiffness. The bars allow good axial stiffness and the cutouts allow bending flexibility. In the case of the helix, because there is not a lot of axial support, this antenna may not be able to puncture tissues as easily. The single bar structure or any other slotted structure would have performances between the ring bar structure and helix. However, the helix shows better radiation profiles than the ring bar and the single ring bar configurations. The need for certain mechanical properties may need to be balanced with the radiation pattern outcomes.

The overall antenna assembly 103 of FIG. 1 may be designed materially and structurally to allow for greater flexibility than is available with rigid conducting materials used in traditional antennas that have a small form factor used to access various locations of target tissue. For example, the antenna assembly 103 may need to bend through 10 to 15 mm bends and as low as 5 mm with the ability to recover for insertion straight through a target tissue. In other words, the flexible plastic deformation limit of certain materials in a particular patterned cylinder, such as copper, is reached and the material plastically deforms when placed in tight bends through tissue, leaving the antenna assembly bent and unable to recover. This makes it hard to aim an antenna assembly towards target tissue.

Accordingly, the material used for the structure of the antenna assembly 103 and any antenna assembly or antenna body described herein may be selected to improve upon the plastic deformation limit and the ability of the antenna assembly to recover its form and re-straighten after passing through a particularly tight bend. This may be accomplished by the material selection for the antenna assembly 103. In some embodiments, the antenna body may be constructed of a highly elastic first material that is plated with a conductive second material. The first material may be more elastic than the second material. The second material may be plated onto the first material on an external surface of the antenna body, i.e. a surface facing away from the longitudinal axis of the antenna assembly.

The first material may be selected from materials that have highly elastic properties relative to less elastic materials such as copper. For example, the first material may be a beryllium-copper alloy (BeCu), nickel titanium (NiTi), or some other similarly plastic material such as steel. Notably, first material does not need to be conductive for emitting radiation at any wavelengths. This is enabled by the plating of the second material onto the first material. The second material may be a conductive material to enable the operation of the antenna assembly as a radiating antenna for ablation of tissue. For example, the second material may be a silver plating or a gold plating onto the material selected as the first material. The relative thickness of the plating for the second material may depend on the frequency or frequencies of operation for the flexible antenna system 100. In some examples, the frequency may be on the order of megahertz to gigahertz, for example approximately 900 MHz to approximately 8 GHz. For example, operation may be selected to be at approximately 2.45 GHz. At such frequencies, the skin depth of the second material may be sufficiently small, such as on the order of microns, that the plating does not have to be very thick. Therefore, the flexibility of the antenna assembly 103 remains intact from the characteristics of the first material.

As a result of the material selection and selection of the appropriate structural patterning, the antenna assembly 103 and any antenna assembly or antenna body described herein maintains a flexible plastic deformation limit that exceeds the strain imposed on the materials of the antenna assembly while working through a tight bend in a lumen. The antenna assembly and particularly the antenna body 108 is therefore able to recover its original form/shape after exiting such a luminal bend, in contrast to existing copper or other materials that would remain deformed due to the lower plastic deformation limits of such materials. As noted above, the antenna tip (e.g., antenna tip portion 104) may be formed from the same or different materials as the antenna body 108.

The patterned structure formed in the tubular antenna body according to the different approaches described herein may also contribute to the flexibility of the antenna body. The resilience and flexibility of the antenna body is demonstrated, for example, in the illustration of FIG. 6A, which provides a simplified diagram of a flexible antenna system 600 (e.g. similar to system 100) in a succession of unbent, bent and recovered states.

Figure 6:
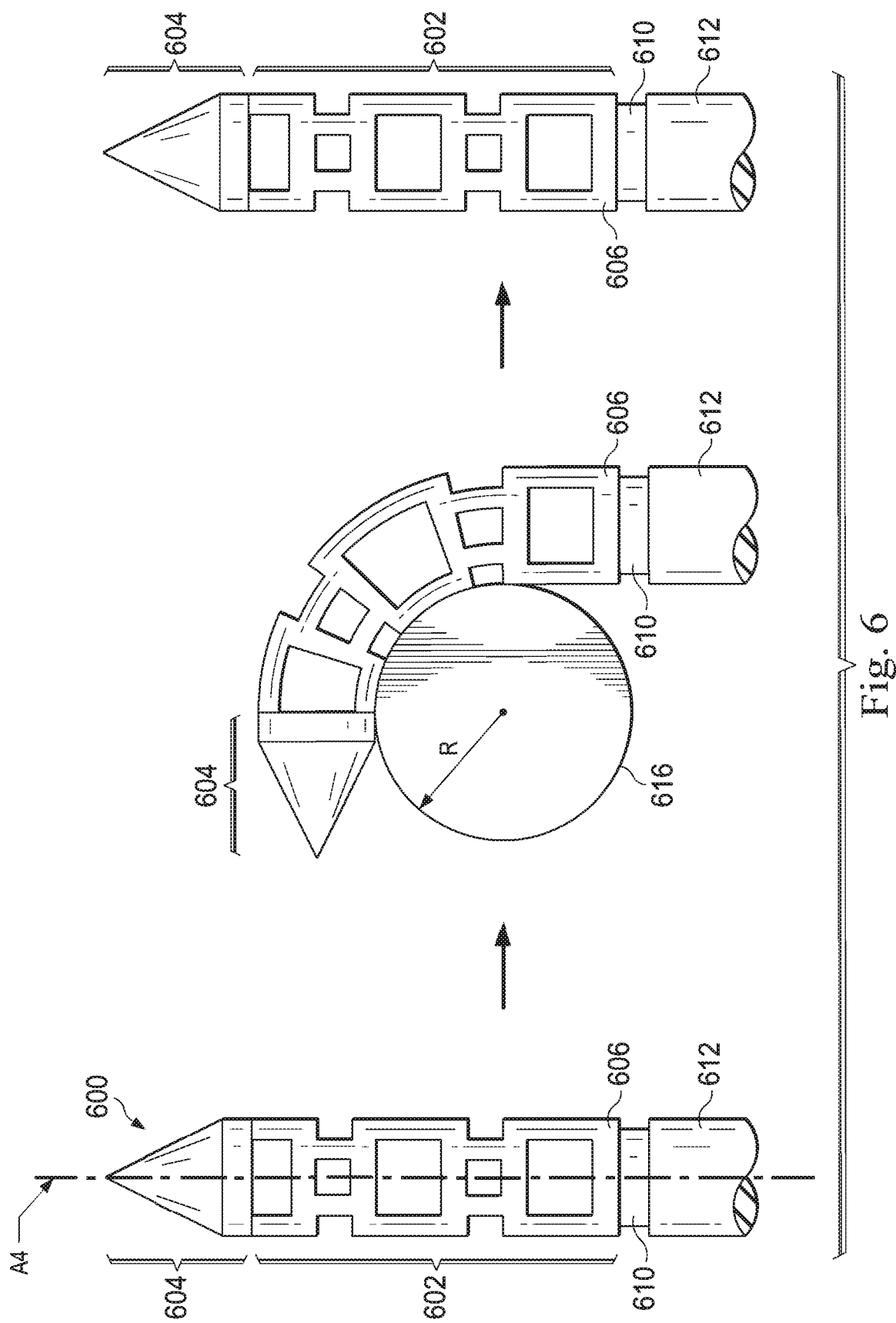
FIG. 6 is a simplified diagram of a flexible antenna system in application around a bend according to some embodiments.

As illustrated, the antenna assembly 600 includes an antenna body 602 coupled to an antenna tip portion 604 and an antenna base 606 coupled to an outer conductor 610 with a jacket 612. In FIG. 6, the antenna assembly 600 begins in the unbent state with a straight configuration along a longitudinal axis A4 (e.g., its default configuration). The antenna assembly 600 may be inserted into anatomic passageways in a patient via a flexible and/or steerable elongate device, such as a flexible catheter, and navigated toward a region of interest within the patient anatomy.

In the example illustrated in FIG. 6, as the antenna assembly 600 is navigated toward the region of interest, it may be subject to forces that place it in a bent state. As illustrated, the antenna assembly 600 is bent around a radius R 616 curve. The radius R 616 of the curve may be on the order of 5 to 20 mm or as small as 5 mm, and the antenna assembly 600 is able to bend around this radius R 616 because it is formed of the first material selected due to its relatively high elastic properties. The patterned structure of the antenna body may also contribute to the elasticity of the antenna assembly.

After the antenna assembly, and particularly the antenna body 602, finished pushing through the bend of radius R 616, the antenna assembly straightens out, recovering and re-straightening back to approximately the antenna body's original shape. This recovered state allows the antenna assembly to approach the target tissue with a predicable trajectory. In some embodiments, the original body shape is a substantially straight shape. In other embodiments, the original body shape if a curved shape allowing for a curved insertion trajectory. This, again, is possible due to the material selected as the first material, and the antenna assembly is able to ablate tissue from energy emitted from the antenna body 602 due to the conductive second material plating the flexible first material. Once in the tissue, power is applied at a particular frequency in either CW or pulsed mode to perform the ablation.

In addition to the flexible aspects of the present disclosure, embodiments of the present disclosure also provide for controlling tissue ablation parameters by controlling one or more parameters of an antenna body. Different parameters affect the resonant frequency of the antenna including the length of the antenna body, number of repetitions within a pattern, angle of cuts in the pattern, materials, tubing diameter and wall thickness, etc. These parameters may be used to affect an ablation zone size created by the flexible antenna system in operation. For example, the length of the antenna body may be referred to as an active length and may include or be defined by a length of the patterned section of the patterned cylindrical structure of the antenna body (e.g., antenna body 108 or any of the alternatives described herein). The patterned section of the antenna body is where most of the energy dissipates for tissue ablation, although some energy will also be dissipated from the respective ends of the antenna structure. Therefore, altering the active length may alter the resonant frequency of the antenna assembly, altering the delivery of ablation energy, and thus altering the ablation zone size during treatment. As another example, the number of repetitions of the pattern for the patterned cylindrical structure describes the spacing between portions of the antenna body. This may be referred to generally as a pitch between the antenna body elements, namely the cutout space between the material of the antenna body (resulting in a total number of antenna body elements within the overall active length). Further, the wall thickness refers to a thickness of the first and second materials of the patterned cylindrical structure together as seen from a cross sectional end view.

For example, referring to the double bar ring embodiments as illustrated in FIG. 5A, as the length of a bar 402 increases (e.g., length D1 increases), a center frequency is reduced. Further, as the rings 401 get longer (i.e., length D2 increases) the center frequency is again reduced. The span of a bar 402 is the circumferential length of the bar. For example, a bar with a span of 90 degrees would span a quarter of the distance around the axis A1 if the bar is viewed in a cross section perpendicular to the axis A1. As the span of each bar is increased, the center frequency is reduced. Finally, decreasing the thickness of the walls of the antenna body decreases the center frequency. The converse would result in increasing the center frequency for each parameter. More generally, changing the different parameters of the antenna assembly may have a varying impact depending on the particular antenna structure, i.e. double bar ring, single bar ring, helical, etc.

Thus, according to embodiments of the present disclosure, the pitch, effective current path length, wall thickness, and cut pattern are different inter-related dimensions of the antenna body that provide extra degrees of freedom from which to control one or more parameters including resonant frequency, maximum allowable strain seen on the antenna assembly, and the ablation size. For example, in the case of the helical antenna body of FIG. 5C, an effective current path length 440 is determined directly by the chosen center frequency; usually it is chosen as a quarterwave length. A structure length SL will define the size of the ablation zone. In so far as they affect the effective current path length 440, the pitch P and the cut pattern also affect the center frequency and should be chosen to produce the necessary current path length and the appropriate structure length. For instance, in a helical antenna of FIG. 5C, the pitch P, number of turns, and radius R of the turns can be used to adjust the maximum strain on the antenna when at a bend and also set so that the ablation zone is the desired size.

For example, the maximum strain on the antenna may be adjusted by increasing the diameter of the patterned cylindrical structure. There is often a practical limit to how much the diameter may be increased due to the size limitations of a delivery device working channel, e.g. a delivery device such as a flexible and/or steerable elongate device, such as a flexible catheter, inserted into anatomic passageways and navigated toward a region of interest within the patient anatomy. Alternatively, the maximum strain may be reduced by decreasing the pitch between turns of an antenna body. This impacts the ablation zone size as well, which may be mitigated by, for example, increasing the effective current path length by increments of $\lambda/2$ while also adjusting the pitch.

Figure 7:
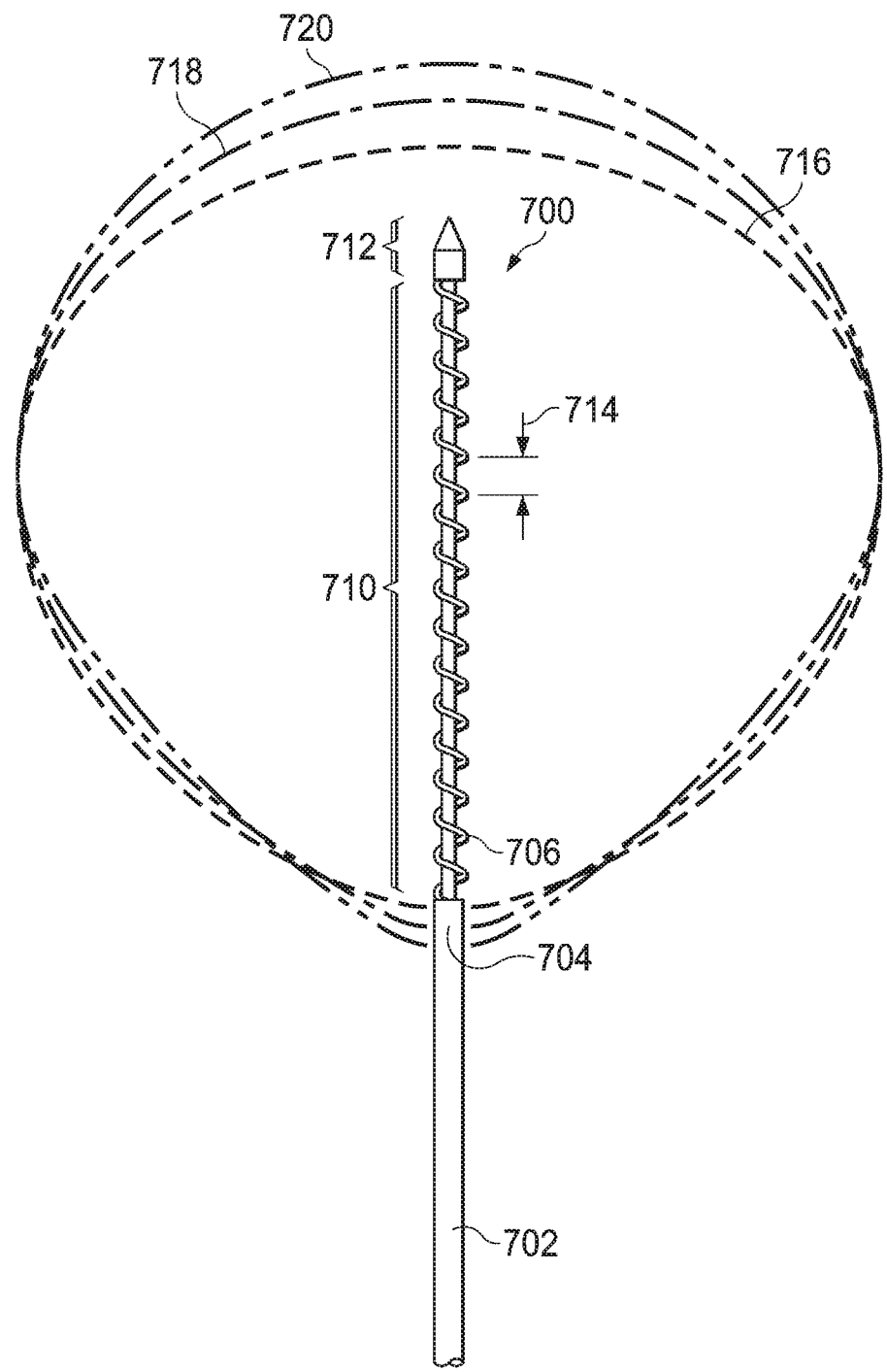
FIG. 7 is a simplified diagram of different ablation patterns for a flexible antenna system according to some embodiments.

Some exemplary effects of patterns and their parameters that may affect ablation zone size are illustrated in FIG. 7. In FIG. 7, a flexible antenna system 700 includes a cable 702, an antenna body 710 (e.g., substantially similar to the antenna body 108 or any of the other antenna bodies described herein). An antenna base 706 of the antenna body 710 is coupled to the distal end 704 of the cable 702. The illustration further shows the antenna tip portion 712, and identifies the varying pitch 714 (referring generally to a spacing between elements of the antenna body 710).

Several different radiation patterns 716, 718, and 720 are illustrated for purposes of discussion. Looking at a variety of different parameters relating to the antenna assembly, the current path length of the antenna body 710 has a relatively large influence on the resonant frequency and bandwidth for the antenna's radiation pattern compared to other parameters. in the case of the helical configuration, the current path length is the length of the unwrapped spiral and has the largest influence on the resonant frequency.

The structure length, i.e. the overall length of patterned portion of the antenna body 710, (i.e. in the case of the helix, the helix length) has a relatively smaller influence on the resonant frequency as compared to the effective current path length. By adjusting the pitch of the repeated elements (i.e. the spirals), we can achieve different effective current path length of antenna with the same resonant frequency.

Generally, the longer the length of the antenna body 710, the longer the ablation lesion length (e.g., in a length parallel to the axis along which the antenna assembly extends from proximal to distal end) in the target tissue, while the ablation lesion width (in a plane transverse to that running parallel to the antenna assembly) remains generally the same. Thus, by increasing the pitch 714, the length of the ablation zone size changes. For example, at a given starting pitch 714, the radiation pattern 718 results (and, therefore, ablation zone size corresponding to the radiation pattern 718. By increasing the pitch 714 (making it larger), the radiation pattern changes to radiation pattern 720, which is longer in the parallel axis and generally the same width in the transverse axis. In contrast, by decreasing the pitch 714 (making it smaller), the radiation pattern changes to radiation pattern 716 which is shorter in the parallel axis as compared to the radiation pattern 718 (but still generally the same width in the transverse axis).

With the configurations of the flexible antenna system discussed herein, embodiments of the present disclosure therefore provide the ability to tailor the ablation zone size in target tissue during ablation. This is in contrast to monopole antennas, where the length of the wire, and the corresponding ablation size in tissue, are both set by the operating frequency.

Several different examples are discussed in further detail below that provide for adjusting one or more parameters of the antennas in order to affect ablation zone size (i.e., tailor the size), maximum strain on the antenna, a combination of both, and/or other parameters.

Figure 8A:
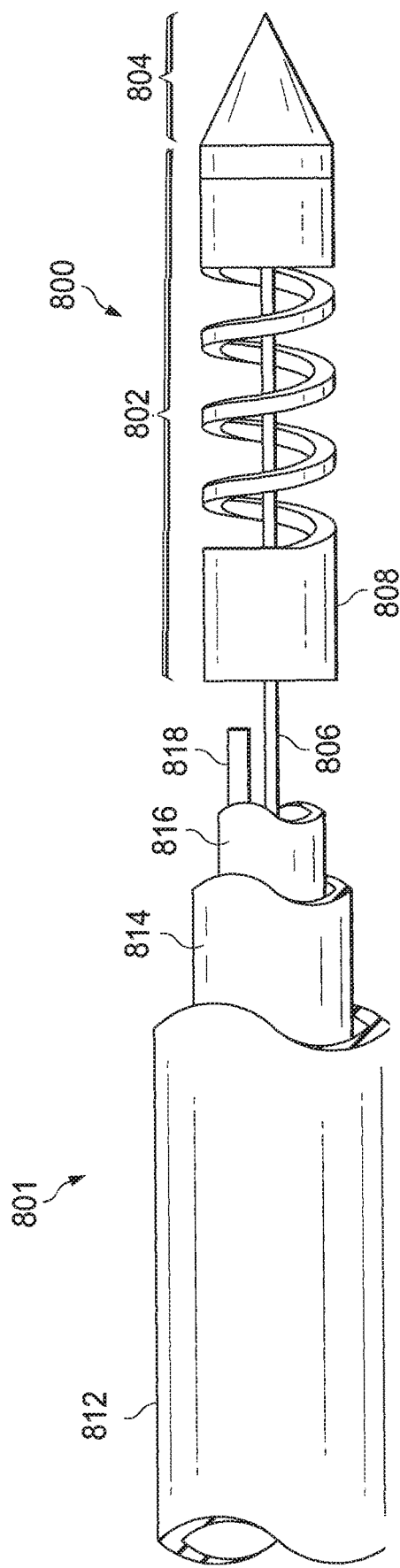
FIG. 8A is a simplified diagram of a flexible and adjustable antenna system according to some embodiments.

FIG. 8A is a simplified diagram of a flexible and adjustable antenna system 800 according to some embodiments. The adjustable antenna system 800 illustrated in FIG. 8A includes many substantially similar elements to those discussed above with respect to the flexible antenna system 100 or other embodiments disclosed herein with the differences as explained. In FIG. 8A a cable 801 is a coaxial cable with a jacket 812, outer conductor 814, dielectric insulator 816, and inner conductor 818. The antenna system 800 includes an antenna base 808, antenna body 802, and antenna tip portion 804.

A push/pull element 806 extends through the cable 801, for example through a passage created in the dielectric insulator 816 that runs approximately parallel to the inner conductor 818 (but which is not in contact with the inner conductor 818). The cable may be a hollow coaxial cable to accommodate the push/pull element 806, or alternatively the push/pull element 806 may be located off-center from the inner conductor 818.

In the illustrated embodiment, the antenna assembly comprising antenna body 802 and antenna tip portion 804 may be electrically (and mechanically) attached to either the inner conductor 818 or the outer conductor 814, while the push/pull element 806 extends through the center of the antenna body 802 and connects with the antenna tip 804 at the distal end of the antenna assembly. This mechanical connection at the antenna tip 804 allows the push/pull element 806 to exert a push and/or pull force on the antenna tip 804, for example provided by a user of the flexible antenna system according to embodiments of the present disclosure.

In some embodiments, the push/pull element 806 extends along the entire length of the cable and is mechanically controlled at the proximal end of the cable along with other aspects of the flexible and/or steerable elongate device (e.g., a manual control or a robotic control using a motor or other actuator). Thus, when a user pushes on the push/pull element 806 at the proximal end, e.g. by physically pushing or pulling on the proximal end of the push/pull element 806 at a location outside of the proximal end of the cable, this is mechanically transferred along the length of the cable to a distal portion of the antenna assembly and the connection to the antenna tip 804.

In an alternative embodiment, the push/pull element 806 does not extend along the entire length of the cable. Instead, a small motor or other actuator or electric interface may be placed at a location in or on the cable closer to the distal end of the antenna assembly, at which point the push/pull element 806 extends the rest of the way to the antenna tip 804. For example, the small interface may be electrically coupled to a controller at the proximal end of the cable, and actuate in response to command signals sent from the controller to push the push/pull element 806 or pull it, depending on the command signals received. In other embodiments, the push/pull element 806 may be formed from a shape memory allow, such as nitinol, such that the shape may be altered when a current is applied (such as per a command signal from a controller).

By actuating the push/pull element 806, the length of the antenna body 802 may be altered, either by elongating the antenna body 802 (when pushing the push/pull element 806 in the distal direction) or compressing the antenna body 802 (when pulling the push/pull element 806 in the proximal direction). This changes the pitch between turns of the antenna body 802 as well as the overall length of the patterned cylindrical structure. This, in turn, dynamically changes delivery of energy and accordingly changes ablation zone size. In the process of changing the pitch length, the center frequency of operation also changes. That change in the center frequency of operation may be addressed by shifting the operating frequency to reduce reflected power due to impedance mismatches.

Figure 8B:
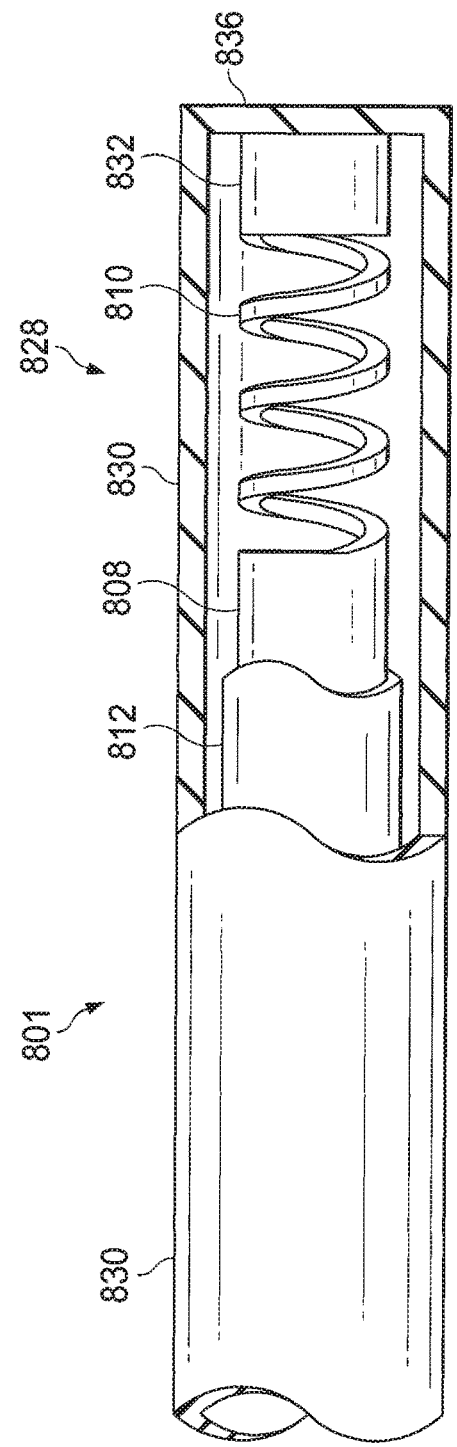
FIG. 8B is a simplified diagram of a flexible and adjustable antenna system according to some embodiments.

FIG. 8B is a simplified diagram of a flexible and adjustable antenna system 828 according to some alternative embodiments. The adjustable antenna system illustrated in FIG. 8B includes many substantially similar elements to those discussed above with respect to the flexible antenna system generally. For example, in FIG. 8B the coaxial cable 801 is used. The antenna assembly system 828 includes the antenna base 808, the antenna body 810, and an antenna tip portion 832.

This embodiment also includes an outer sheath 830. The outer sheath 830 surrounds the rest of the cable as well as the antenna assembly, and is able to slide longitudinally relative to the cable (generally parallel to the axis of the cable) and the antenna assembly. As can be seen from FIG. 8B, the antenna assembly has a blunt antenna tip portion 832 (e.g., a square end, an elliptically shaped end, etc. with or without rounded edges), with a sufficient area to come in contact with a sheath tip 836 at the distal end of the assembly.

The outer sheath 830 may encapsulate the full length of the cable, and thus extend from the proximal end of the cable to the distal end where the antenna assembly is located along with other aspects of the flexible and/or steerable elongate device. The outer sheath 830 may be controllable to move in response to a push or pull action. The push or pull action may, in such embodiments, be applied at the proximal end and translated along the length of the cable until it is applied to the antenna tip portion 832 by the sheath tip 836.

In some alternative embodiments, the outer sheath 830 does not extend the full length of the cable, but rather instead may be controlled by a small motor or other electric interface placed at a location on or in the cable closer to the distal end of the antenna assembly. For example, the small interface may be electrically coupled to a controller at the proximal end of the cable, and actuate in response to command signals sent from the controller to push the outer sheath 830 away from the antenna tip portion 832, or pull the outer sheath 830 against the antenna tip portion 832, depending on the command signals received.

In operation, pulling the outer sheath 830 towards the proximal direction causes the sheath tip 836 to press against some or most of the surface of the antenna tip portion 832. This, in turn, applies a compressive force against the antenna tip portion 832 (e.g., since the movement of the outer sheath 830 does not occur with any corresponding movement of the cable within the outer sheath 830), which decreases the pitch of the helical antenna body 802 and, therefore, the ablation zone size (e.g., a smaller length).

In another example, pushing the outer sheath 830 towards the distal direction away from the antenna tip portion 832 causes the sheath tip 836 to relax the force applied against the antenna tip portion 832. In some embodiments, the sheath tip 836 and the antenna tip distal end 832 are not mechanically joined together, but rather are only in physical contact with each other depending on the amount of force applied by the sheath tip 836. Thus, as the sheath tip 836 is extended distally, this reduced the amount of force applied by the sheath tip 836 against the antenna tip portion 832, which may allow the antenna body 810 to expand, therefore increasing the pitch 714 between cutouts and correspondingly altering energy delivery to increase ablation size.

In some other embodiments, the sheath tip 836 and the antenna tip portion 832 are mechanically joined together, such as by adhesive. Thus, when the sheath tip 836 is extended distally, instead of just releasing some of the force previously applied against the antenna tip portion 832, the movement of the sheath tip 836 exerts a force in the distal direction that pulls the antenna tip portion 832 towards the distal direction. This again increases the pitch 902 to change the pitch length, modify the center frequency of operation, and thus modifying the ablation zone size. That change in the center frequency of operation may be addressed by shifting the operating frequency should too much power be reflected at the interface between the conductor (inner or outer) electrically connected to the antenna assembly.

In some embodiments, movement of the outer sheath 830 may be tele-operationally controlled by coupling the sheath to an actuator located along the length of the antenna system or at a proximal end of the antenna system.

FIGS. 9A-9C illustrate simplified diagram of a flexible and adjustable antenna system 900 according to some embodiments. As illustrated in FIG. 9A, the antenna assembly 905 includes a distal end 903 and an antenna body 905 formed from two distinct portions, inner tube 902 and outer tube 904. These tubes 902, 904 are slidable with respect to each other as will be discussed in more detail below. Each of the inner and outer tubes 802, 804 may be formed from a nonconductive, flexible, elastic material that has a plastic deformation limit greater than the amount of strain placed on the material when traversing, e.g., a 5 mm bend in a tortuous pathway. For example, one or both of the inner and outer tubes 802, 804 may be formed from a material such as BeCu, NiTi, or steel as just a few examples. The inner tube 902 may include conductive traces along an outer surface of the inner tube 902, while the outer tube 904 may include corresponding conductive traces along an inner surface of the outer tube 904. Accordingly, electrical connections between the inner and outer tubes 902, 904 may occur when the relative positioning of the inner tube to the outer tube aligns the conductive traces.

The conductive traces are illustrated as a first pattern 908a on the outer surface of the inner tube 902—in particular, etched, engraved, printed on, adhered to, or otherwise secured to the outer surface of the inner tube 902. The first pattern 908a is illustrated as being a spiral around the outer surface of the inner tube 902 extending from a first inner contact 906a at a distal end of the inner tube 902 to a second inner contact 906b at a proximal end of the inner tube 902.

Likewise with respect to the outer tube 904, conductive traces are etched/engraved/printed/adhered/etc. as a second pattern 908b on the inner surface of the outer tube 904. The second pattern 908b is illustrated as being a spiral around the inner surface of the outer tube 904 extending from a first outer contact 910a at a distal end of the outer tube 904 to a second outer contact 910b at a proximal end of the outer tube 904, where the flexible and adjustable antenna system 900 connects to the cable 901.

According to some embodiments, either the first pattern 908a or the second pattern 908b is electrically connected by default to a conductor of the cable to receive electrical energy to generate radiation patterns (FIG. 7) for tissue ablation. Thus, the connected pattern receives the electrical energy and generates the radiation pattern to cause the ablation zone size, as set by the pitch of the pattern. For example, if the second pattern 908b on the outer tube 904 is the one connected by default, then the radiation pattern is generated according to the parameters of the second pattern 908b.

As illustrated in FIG. 9B, the flexible and adjustable antenna system 900 is in a first configuration 900a according to some embodiments. The inner tube 902 is shown positioned within the hollow outer tube 904, but in a configuration such that the first inner contact 906a is not in electrical contact with the first outer contact 910a, and likewise the second inner contact 906b and the second outer contact 910b. Thus, only the tube that is electrically connected by default to an energy source generates a radiation pattern, and therefore an ablation zone size, via the pattern. The default connection is with the second pattern 908b on the outer tube 904. Thus, the radiation pattern generated is from the parameters, such as pitch, length, etc. of the second pattern 908b.

If it is desired to control/adjust the ablation zone size, then a user may adjust the flexible and adjustable antenna system 900 to a second configuration 900b, as illustrated in FIG. 9C. According to the example illustrated in FIG. 9C, the inner tube 902 has been rotated relative to the outer tube 904 so that the contacts are now over each other to some degree, providing an electrical connection between respective contacts on the inner and outer tubes 902, 904. In alternative embodiments, the relative position of the inner tube 902 to the outer tube 904 may be altered by altering a relative longitudinal position of the inner tube 902 to the outer tube 904 or a combination of altering the relative longitudinal position and relative rotational positions of inner tube 902 to outer tube 904.

When adjusted to the second configuration 900b, the first inner contact 906a is now overlapping at least part of the first outer contact 910a, and the contacts are sufficiently close to each other so as to be in electrical and physical contact with the other. Likewise, the second inner contact 906b is now overlapping at least part of the second outer contact 910b, with the contacts sufficiently close to each other so as to be in electrical and physical contact with the other. Therefore, the first pattern 908a, which was not in electrical contact with the energy source previously as was the second pattern 908b's default connection, is now also in contact with that energy source.

As a result, the first pattern 908a is now conducting energy via the first and second inner contacts 906a, 906b being in connection with the corresponding first and second outer contacts 910a, 910b. Thus, electrical energy may now flow between the first and second inner contacts 906a, 906b via the first pattern 908a. As can be seen, since both the inner and outer patterns 908a, 908b are now conducting, both are contributing to the radiation pattern of the antenna assembly. This effectively reduces the pitch and increases the length of the radiating antenna, as both first and second patterns 908a, 908b contribute to the radiation pattern.

Although illustrated as just two patterns on the inner and outer tubes, embodiments of the present disclosure are also applicable to any number of different patterns and configurations, such that the tubes may move relative to each other to more than two different configurations to achieve more unique parameter combinations to change the radiation pattern contributing to the tissue ablation zone size.

The inner tube 902 is adjusted relative to the outer tube 904, the outer tube 904 is adjusted relative to the inner tube 902, or both tubes are adjusted relative to one another. The tubes may be manually adjusted from a proximal end or robotically actuated. For example, the tubes may have a set track on which they may twist between the first and second positions, with guides to indicate (e.g., via some form of tactile or electronic feedback) that the first or second positions have been reached.

The above examples, e.g. with respect to FIGS. 8A-9C, describe dynamic control/adjustment of the parameters contributing to the tissue ablation zone size for ablation. In other embodiments, this control/adjustment may be done statically, e.g. a set of antennas with varying parameters, e.g. antenna body length, pattern, pitch, radius, wire diameter, and material may be available and delivered for ablation depending on a desired ablation zone size.

Figure 14:
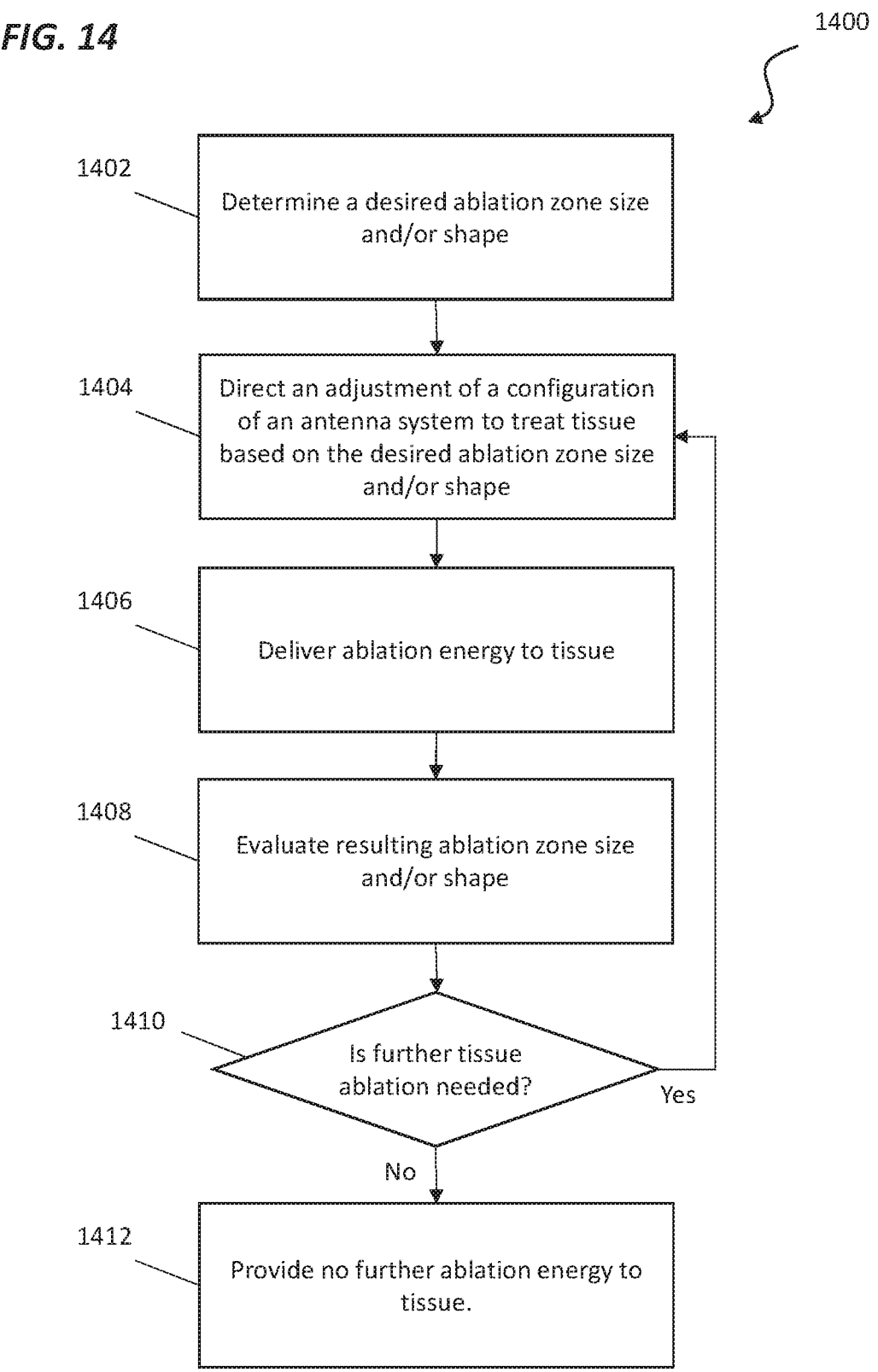
FIG. 14 is a method for adjusting parameters for ablation size and location according to some embodiments.

FIG. 14 illustrates a method 1400 for adjusting parameters for ablation size and location according to some embodiments. It is understood that additional processes can be provided before, during, and after the processes of method 1400 and that some of the processes described can be replaced or eliminated from the method 1400. The method 1400 may be manual or may be controlled by a processor of a control system (e.g., a control system 1112). At a process 1402, a desired ablation zone size and/or shape is determined, for example, by using external imaging techniques such as MRI, CT, ultrasound, or fluoroscopy; internal imaging techniques such as endobronchial ultrasonography (EBUS), intravascular ultrasonography (IVUS), optical coherence tomography (OCT); or a user input. At a process 1404, an adjustment of a configuration of the antenna system to treat tissue based on the desired ablation zone size and/or shape may be directed manually by a user or tele-operationally by the control system 1112 of an adjustment mechanism. The configuration of the antenna system may be adjusted by adjusting one or more antenna parameters including antenna body length, pattern, pitch, radius, wire diameter, and material; and/or system parameters including cooling flow rate, ablation time, power, duty cycle, frequency, max temperature, and other energy characteristics; and/or position/orientation of the antenna. In some embodiments, the adjustment may be tele-operationally controlled by the control system 1112. In other embodiments, the control system 1112 may provide instructions (e.g., via a display system or audio system) to instruct a user on making adjustments to the antenna system, including replacing antenna system components. At a process 1406, ablation energy is delivered to the tissue with the antenna system having the adjusted configuration. At a process 1408, an ablation zone size and/or shape, resulting from the delivered ablation energy, is evaluated. The evaluation may be conducted using external imaging techniques such as MRI, CT, ultrasound, or fluoroscopy; internal imaging techniques such as EBUS, IVUS, or OCT. Alternatively, the evaluation maybe conducted using measured impedance or other electrical properties of the tissue. At a process 1410, based on the evaluation a determination is made regarding whether further tissue ablation is needed. If further ablation is needed, processes 1404-1410 may be repeated with the antenna system repositioned or re-oriented, as needed. If no further ablation is needed, no further ablation energy may be provided at process 1412.

In some embodiments, an impedance mismatch and unwanted reflections at an interface between the cable and the antenna assembly may occur. To avoid these issues, a matching network may be applied. For example, a quarter wave transformer may be formed by changing the diameters of the inner conductor or dielectric. For instance, 30 Ohm cable could be used to impedance match. The quarter wave section may be formed by thinning the inner conductor 326 by ablation, necking, or joining another section of coaxial cable with a corresponding inner conductor 326 of a different size. Alternatively, the outer diameter of the cable may be increased or decreased to create the quarter wave transformer, though this also reaches size limitations due to the size limitations of the working channel.

In some embodiments, given possible challenges in thinning the inner conductor 326 to the appropriate diameter at the interface, the quarter wave transformer may be created by instead using a high dielectric constant material such as highly doped titanium dioxide ($TiO_2$) in the polymer (e.g., polytetrafluoroethylene, or PTFE) of the sheath.

With respect to unwanted current propagation down the outside of the coax shaft, a choke or balun can be used to attenuate the electric field and not burn unnecessary tissue. Such chokes include bazooka baluns, or other sections of conductive tubing concentric to the outer conductor of the cable that are either floating or connected to the outer conductor in the proximal or distal ends. A double balun or choke can also be used; this structure is formed from two of the previously described structures for more current suppression. The dielectric between the choke/balun and the outer conductor can be plastics, water, ceramics, or any insulating material.

A second choice for attenuating unwanted currents is to utilize a highly resistive surface coating on the surface of the outer conductor. This can be painted, deposited, or otherwise applied to various sections of the outer conductor. Additionally, materials of lower conductivity could be spliced in the right places to the outer conductor to achieve a similar effect, such as graphene or aquadag for example.

Figures 10A, 10B:
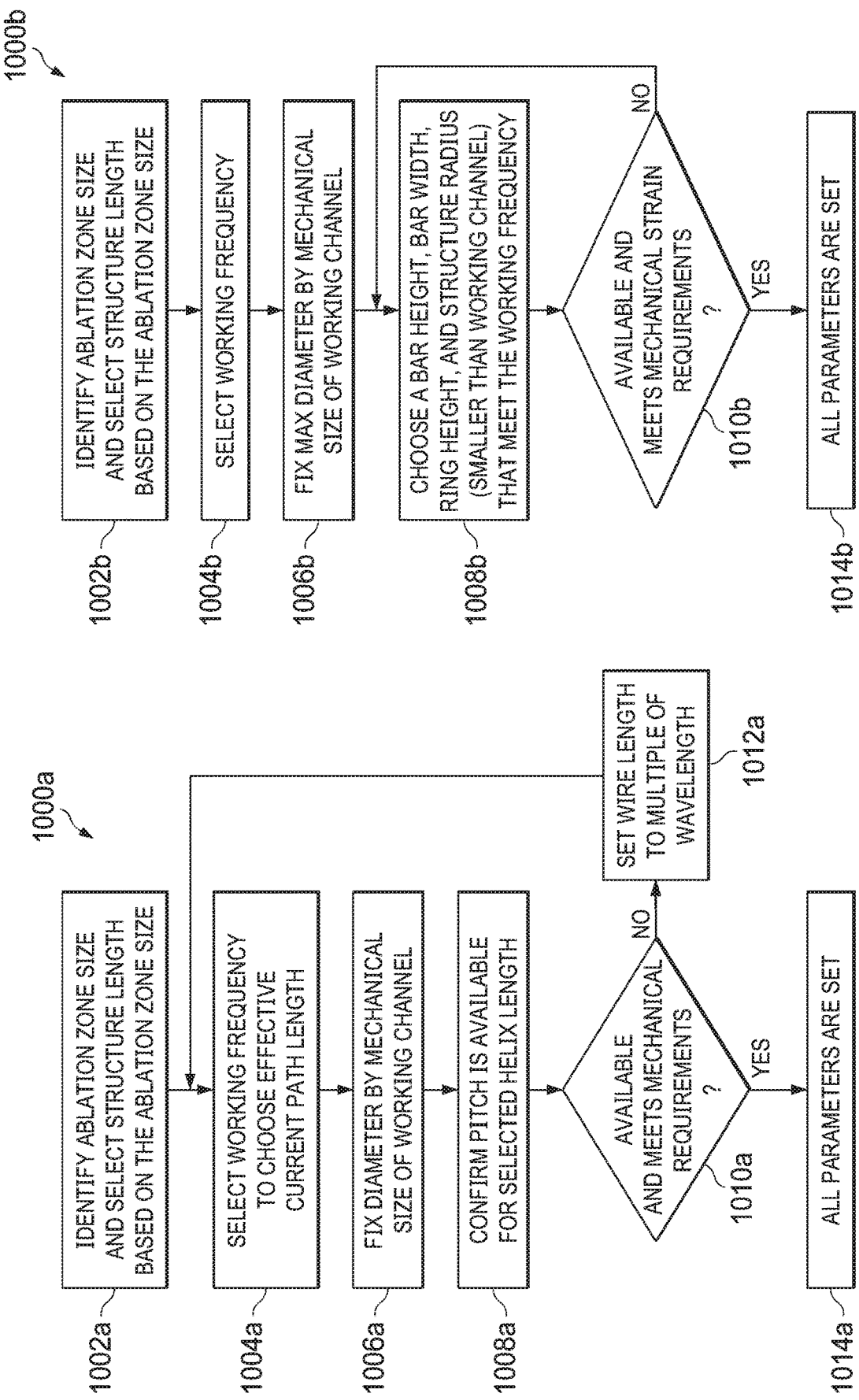
FIGS. 10A and 10B is a method diagram for configuring a flexible antenna system according to some embodiments.

Turning now to FIG. 10A, a method diagram 1000a is illustrated for designing a flexible helical antenna system according to some embodiments. In particular, the method 1000a illustrates aspects of configuring (e.g., including optimizing) the flexible antenna system 100 according to embodiments of the present disclosure. The discussion is also applicable to the various antenna body configurations. It is understood that additional steps can be provided before, during, and after the steps of method 1000a, and that some of the steps described can be replaced or eliminated from the method 1000a.

At block 1002a, the ablation zone size is identified or chosen that is desired for tissue ablation. With the ablation zone size identified/chosen, the structure length that creates radiation patterns to achieve just under the identified ablation zone size is selected.

At block 1004a, a working frequency is selected, which informs what the appropriate current path length. In the example of a helix, this corresponds to the unwrapped length of the helix. The length will be, for example, some multiple of a quarter or half wavelength depending on whether operation is at the first resonant frequency or the second resonant frequency (either of which is allowed according to embodiments of the present disclosure).

At block 1006a, the diameter of the antenna body 108 (e.g., FIG. 1) is fixed based on the determined mechanical size of the working channel through which the antenna body 108 will traverse in use. For example, the working channel may be through a flexible and/or steerable elongate device, such as a flexible catheter, inserted into anatomic passageways and navigated toward a region of interest within the patient anatomy.

At block 1008a, the other parameters of the device and the pitch and number of repetitions is selected to correspond to the selected ablation length. For example, in the case of the helix, there will be confirmation that the windings for the selected helix length would not be too short for convenient regular operation as an antenna for tissue ablation).

At decision block 1010a, if the pitch is available and meets the necessary mechanical strain requirements, then the method 1000a proceeds to block 1014a.

At block 1014a, the pitch is set to the value determined at block 1008a and all parameters are fixed Returning to decision block 1010a, if the pitch is not available (e.g., too short for practical purposes), then the method 1000a instead proceeds to block 1012a. At block 1012a, the length used at block 1004a is changed to a multiple of the wavelength of the working frequency selected previously at block 1004a.

From there, the method 1000a returns to block 1006a and proceeds again as laid out above. Accordingly, the antenna may be optimized according to embodiments of the present disclosure, including by selection of the flexible material for the coil substrate (plated over with a conductive material), and including adjustability of the parameters of the flexible antenna system 100 to achieve different radiation patterns (FIG. 7).

FIG. 10B illustrates a method diagram 1000b for designing a flexible antenna system. Method 1000b may be similar to method 1000a but is used for designing a different patterned antenna body, such as a ring and bar antenna body. In particular, the method 1000b illustrates aspects of configuring (e.g., including optimizing) the flexible antenna system 100 according to embodiments of the present disclosure. The discussion is also applicable to the various antenna body configurations. It is understood that additional steps can be provided before, during, and after the steps of method 1000b, and that some of the steps described can be replaced or eliminated from the method 1000b.

At block 1002b, the ablation zone size is identified or chosen that is desired for tissue ablation. With the ablation zone size identified/chosen, the structure length that creates radiation patterns to achieve just under the identified ablation zone size is selected.

At block 1004b, a working frequency is selected, which informs what the appropriate current path length.

At block 1006b, the maximum diameter of the antenna body is fixed based on the determined mechanical size of the working channel through which the antenna body will traverse in use. For example, the working channel may be through a flexible and/or steerable elongate device, such as a flexible catheter, inserted into anatomic passageways and navigated toward a region of interest within the patient anatomy.

At block 1008b, a ring height, radius, bar height, and bar width, and tube thickness are chosen to meet resonance at the working frequency.

At decision block 1010b, if the ring and bar dimensions are available and meet the necessary mechanical strain requirements, then the method 1000b proceeds to block 1014b. For example, if the strain remains lower than the plastic deformation, the method 1006 proceeds to block 1014b; otherwise the parameters of the antenna are tweaked and the process is repeated.

At block 1014b, the dimensions are set to the value determined at block 1008b and all parameters are fixed.

Returning to decision block 1010b, if the dimensions are not available, then the method 1000b instead returns to block 1010b.

Accordingly, the antenna may be optimized according to embodiments of the present disclosure, including by selection of the flexible material for the substrate (plated over with a conductive material), and including adjustability of the parameters of the flexible antenna system 100 to achieve different radiation patterns (FIG. 7).

Figure 10C:
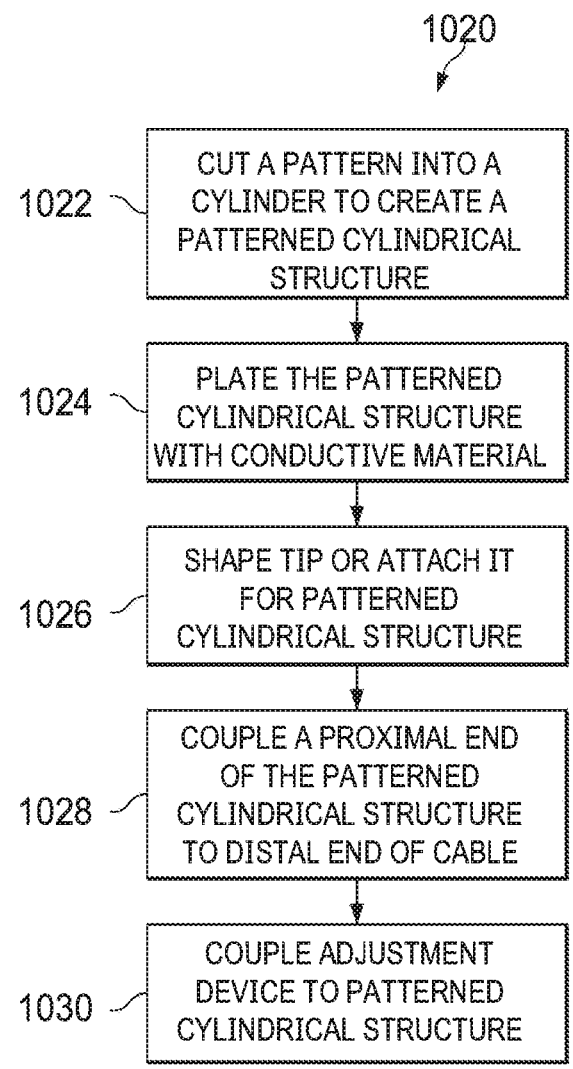
FIG. 10C is a method diagram for manufacturing a flexible antenna system according to some embodiments.

Turning now to FIG. 10C, a method diagram is illustrated for configuring a flexible antenna system according to some embodiments. In particular, the method 1020 illustrates aspects of manufacturing (e.g., assembling) the flexible antenna system 100 according to embodiments of the present disclosure. The discussion is applicable to the various antenna body configurations. It is understood that additional steps can be provided before, during, and after the steps of method 1020, and that some of the steps described can be replaced or eliminated from the method 1020.

At block 1022, a pattern is cut, such as laser cut, into a hollow cylinder. This creates a patterned cylindrical structure, such as the ones introduced above. The hollow cylinder may be composed of a material that has a relatively low conductive property, for example a beryllium-copper alloy (BeCu), nickel titanium (NiTi), or some other similarly plastic material such as steel.

At block 1024, the patterned cylindrical structure is plated with a conductive material to enable the operation of the antenna assembly 103 as a radiating antenna for ablation of tissue. The plating may be, for example, a silver plating or a gold plating. The relative thickness of the plating may depend on the frequency or frequencies of operation for the flexible antenna system 100. Although discussed as occurring after the pattern is cut, in some embodiments the cylinder is plated and then the pattern is cut.

At block 1026, a tip is shaped (optional) for the distal end of the patterned cylindrical structure. For example, the tip may be formed from the material at the end of the patterned cylindrical structure, such as by cutting the end of the open tube into multiple tip sections that are then crimped (e.g., bent at their interface with the remaining material of the flexible antenna system 100 such as that of the antenna body 108), so that the distal portion of each tip section is substantially in contact with the distal portion of the other tip sections to form a cone as the antenna tip, such as discussed with respect to FIGS. 4A and 4B. Alternatively, the tip may be a separate component welded to the distal end of the patterned cylindrical structure (FIG. 4C), held in place by tabs (FIG. 4E) or screwed into each other (FIG. 4D). These are just some examples. Block 1026 may be an optional one in method 1020.

At block 1028, the proximal end of the patterned cylindrical structure, which since it is plated may also be referred to as the antenna assembly 103 according to the embodiments introduced with FIG. 1 herein, is coupled to the distal end of the cable. As part of that coupling, the base of the antenna may be electrically coupled to either the inner or the outer conductor of the cable (in examples where the cable 102 is a coaxial cable). In some embodiments, only one of the conductors is coupled to the antenna; in other embodiments, one of the conductors is coupled to the proximal end of the antenna while the other conductor (e.g., the inner) is coupled to the distal end as well.

In some embodiments, block 1030 then occurs (i.e., this is an optional part of method 1020). At block 1030, an adjustment device is coupled to the patterned cylindrical structure (which is used in operation to change the ablation size of the device by adjusting pitch and/or other parameters of the antenna). This is illustrated as optional in FIG. 10B to recognize that some devices may include this element while others might not. The adjustment device may assume a variety of forms/approaches, such as the examples illustrated in FIGS. 8A-9C. As a result of the above manufacturing method, a flexible antenna system is provided as discussed with respect to embodiments of the present disclosure. The blocks 1024, 1026, and 1030 and the processes described therein may occur in different sequences.

Figure 15:
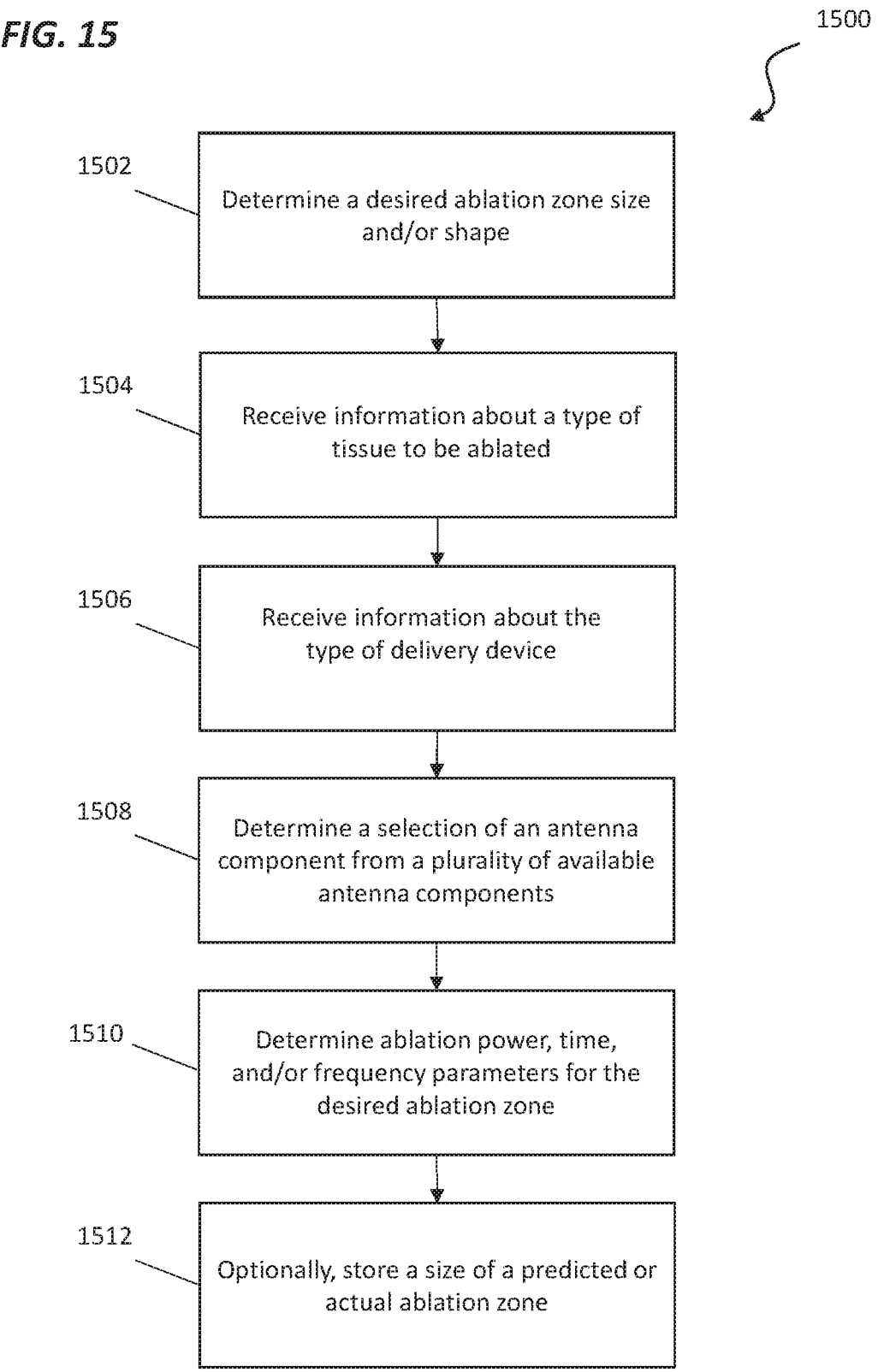
FIG. 15 is a method for antenna component selection according to some embodiments.

FIG. 15 illustrates a method 1500 for antenna component selection according to some embodiments. It is understood that additional processes can be provided before, during, and after the processes of method 1500 and that some of the processes described can be replaced or eliminated from the method 1500. The method 1500 may be controlled by a processor of a control system (e.g., a control system 1112).

At a process 1502, a desired ablation zone size and/or shape is determined, for example, by using external imaging techniques such as MRI, CT, ultrasound, or fluoroscopy; internal imaging techniques such as endobronchial ultrasonography (EBUS), intravascular ultrasonography (IVUS), optical coherence tomography (OCT); or a user input. This process may include receiving information about a location of lesion, such as by user input or by imaging technology. Additionally or alternatively, this process may include receiving information about surrounding anatomical structures such as blood vessels, by user input or by imaging technology.

At a process 1504, information about a type of tissue to be ablated is received. The tissue type may include, for example, lung, stomach, intestine, liver, kidney, kidney stone, bladder, prostate, uterus, ovary, or other types of anatomical tissue. Tissue type may be provided as an input by a user (e.g. by inputting a target organ or intended medical procedure) or automatically identified using imaging techniques (e.g. automatic identification of organs within scans from MRI, CT, ultrasound, fluoroscopy, OCT, etc.).

At a process 1506, information about a type of delivery device (e.g. a flexible elongate delivery device) may be received by the control system for use in determining a size (e.g. a maximum size) of a customizable component of an antenna system to be delivered within a working channel of the delivery device. In one embodiment, the delivery device information can be determined by the control system based the determination of tissue type (e.g. organ and passageway access to the organ) to be ablated. For example, the control system may identify a maximum size of a delivery device based on a type of target organ (e.g. lung, liver, kidney, etc.) to be accessed and size of passageways (e.g. airways, rectum, esophagus, etc.) providing access to the target organ. The control system may then determine the maximum size of an antenna system that can be received within the working channel of the delivery device. At a process 1508, a determination may be made regarding the selection of an antenna component from a plurality of available antenna components. The determination may be made by the control system (e.g., control system 1112). The antenna components may include, for example a plurality of antenna bodies 108 that vary based on physical parameters, for example, helical pitch, wire length, and pattern (e.g., bar height, bar width, ring height, and cut-out pattern). In some embodiments, a visual or audible indicator may provide a user with instructions for selecting the determined antenna component. In some embodiments, as with a robotic system, the antenna component may be automatically chosen. At a process 1510, a determination is made regarding treatment parameters such as ablation power, time, and/or frequency needed to generate the desired ablation zone size and/or shape with the selected antenna component. The determination may be made by the control system (e.g., control system 1112) and may be based on any of the received or determined information including the tissue type and the selected antenna component. At a process 1512, optionally, a size of a predicted or actual ablation zone may be stored. This process may be performed after a delivery of ablation energy to the anatomical tissue. The stored ablation zone may be used to guide a secondary ablation.

In alternative embodiments, after delivering power using the selected antenna, the ablation may be evaluated and the processes 1508, 1510, 1512 may be repeated and further ablation may be conducted at the target anatomical site.

The flexible antenna system according to embodiments of the present disclosure (including flexible and adjustable antenna systems) may be operated in any number of ways, including manually as well as in automated fashion, to ablate target tissue (e.g., using microwave ablation as just one RF example to which these embodiments apply). For automated approaches, robotic systems may be employed for precision targeting of tissue and surgical operation.

To that end, this disclosure describes various instruments and portions of instruments in terms of their state in three-dimensional space. As used herein, the term "position"

refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 11:
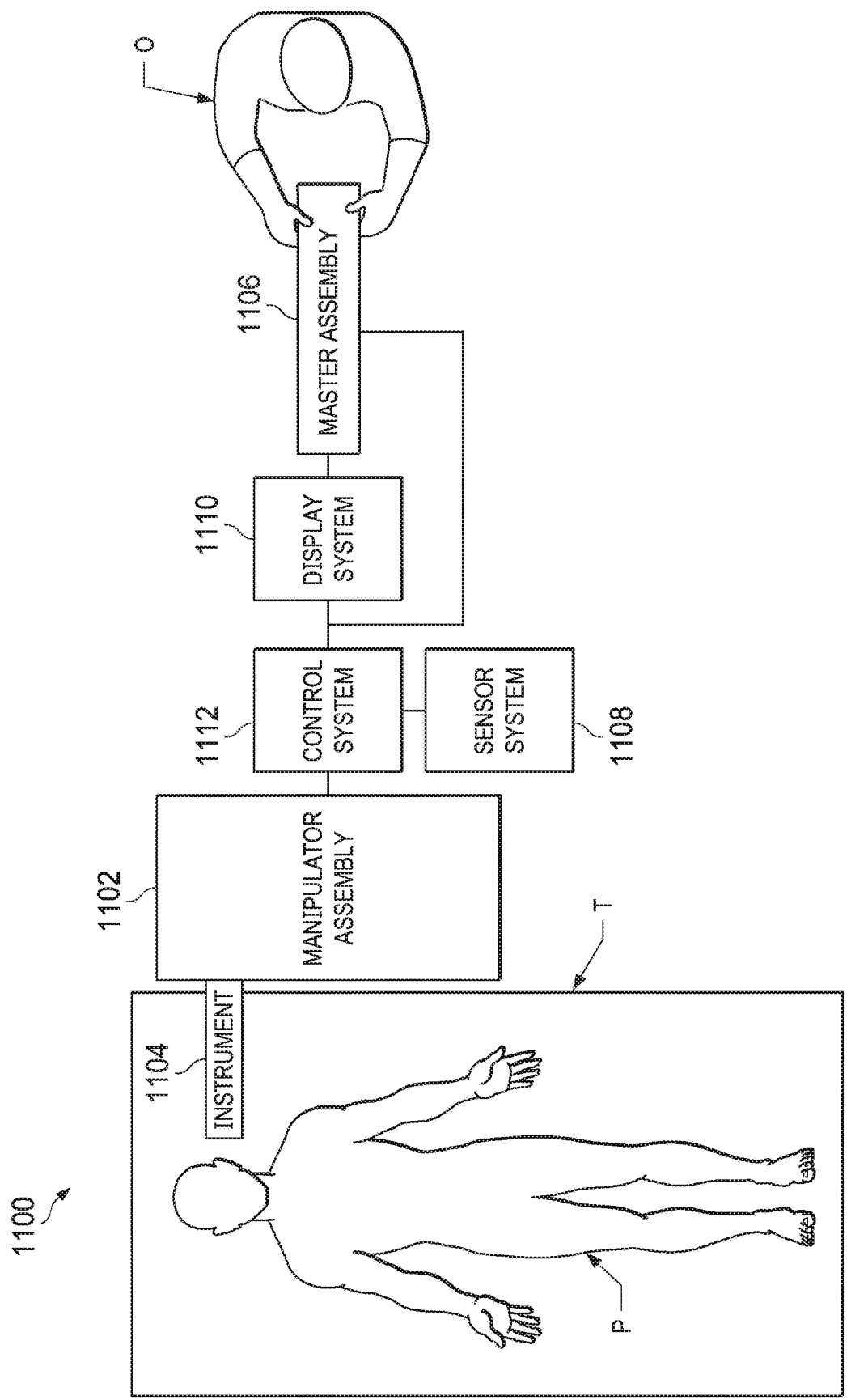
FIG. 11 is a simplified diagram of a teleoperated medical system according to some embodiments.

FIG. 11 is a simplified diagram of a teleoperated medical system 1100 according to some embodiments. In some embodiments, teleoperated medical system 1100 may be suitable for use in, for example, surgical, diagnostic, therapeutic, or biopsy procedures, including tissue ablation (such as tumor tissue ablation). While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 11, medical system 1100 generally includes a manipulator assembly 1102 for operating a medical instrument 1104 in performing various procedures on a patient P (e.g., tissue ablation with a flexible antenna system 100 according to embodiments of the present disclosure). The manipulator assembly 1102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 1102 is mounted to or near an operating table T. A master assembly 1106 allows an operator (e.g., a surgeon, a clinician, or a physician as illustrated in FIG. 11) to view the interventional site and to control manipulator assembly 1102.

Master assembly 1106 may be located at an operator console which is usually located in the same room as operating table T, such as at the side of a surgical table on which patient P is located. However, it should be understood that operator O can be located in a different room or a completely different building from patient P. Master assembly 1106 generally includes one or more control devices for controlling manipulator assembly 1102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 1104 the control devices may be provided with the same degrees of freedom as the associated medical instrument 1104. In this manner, the control devices provide operator O with telepresence or the perception that the control devices are integral with medical instruments 1104.

In some embodiments, the control devices may have more or fewer degrees of freedom than the associated medical instrument 1104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode and/or antenna, delivering a medicinal treatment, and/or the like).

Manipulator assembly 1102 supports medical instrument 1104 and may include a kinematic structure of one or more non-servo controlled links (e.g., one or more links that may be manually positioned and locked in place, generally referred to as a set-up structure), and/or one or more servo controlled links (e.g. one more links that may be controlled in response to commands from the control system), and a manipulator. Manipulator assembly 1102 may optionally include a plurality of actuators or motors that drive inputs on medical instrument 1104 in response to commands from the control system (e.g., a control system 1112). The actuators may optionally include drive systems that when coupled to medical instrument 1104 may advance medical instrument 1104 into a naturally or surgically created anatomic orifice. Other drive systems may move the distal end of medical instrument 1104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 1104 for grasping tissue in the jaws of a biopsy device and/or the like. Actuator position sensors such as resolvers, encoders, potentiometers, and other mechanisms may provide sensor data to medical system 1100 describing the rotation and orientation of the motor shafts. This position sensor data may be used to determine motion of the objects manipulated by the actuators.

Teleoperated medical system 1100 may include a sensor system 1108 with one or more sub-systems for receiving information about the instruments of manipulator assembly 1102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 1104; and/or a visualization system for capturing images from the distal end of medical instrument 1104.

Teleoperated medical system 1100 also includes a display system 1110 for displaying an image or representation of the surgical site and medical instrument 1104 generated by sub-systems of sensor system 1108. Display system 1110 and master assembly 1106 may be oriented so operator O can control medical instrument 1104 (e.g., including tissue ablation via RF, such as microwave frequencies) and master assembly 1106 with the perception of telepresence.

In some embodiments, medical instrument 1104 may have a visualization system (discussed in more detail below), which may include a viewing scope assembly that records a concurrent or real-time image of a surgical site and provides the image to the operator or operator O through one or more displays of medical system 1100, such as one or more displays of display system 1110. The concurrent image may be, for example, a two or three dimensional image captured by an endoscope positioned within the surgical site. In some embodiments, the visualization system includes endoscopic components that may be integrally or removably coupled to medical instrument 1104. However in some embodiments, a separate endoscope, attached to a separate manipulator assembly may be used with medical instrument 1104 to image the surgical site. The visualization system may be implemented as hardware, firmware, software or a combination thereof which interact with or are otherwise executed by one or more computer processors, which may include the processors of a control system 1112.

Display system 1110 may also display an image of the surgical site and medical instruments captured by the visualization system. In some examples, teleoperated medical system 1100 may configure medical instrument 1104 and controls of master assembly 1106 such that the relative positions of the medical instruments are similar to the relative positions of the eyes and hands of operator O. In this manner operator O can manipulate medical instrument 1104 and the hand control as if viewing the workspace in substantially true presence. By true presence, it is meant that the presentation of an image is a true perspective image simulating the viewpoint of a physician that is physically manipulating medical instrument 1104.

In some examples, display system 1110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 1110 may display a virtual navigational image in which the actual location of medical instrument 1104 is registered (i.e., dynamically referenced) with the preoperative or concurrent images/model. This may be done to present the operator O with a virtual image of the internal surgical site from a viewpoint of medical instrument 1104. In some examples, the viewpoint may be from a tip of medical instrument 1104. An image of the tip of medical instrument 1104 and/or other graphical or alphanumeric indicators may be superimposed on the virtual image to assist operator O controlling medical instrument 1104. In some examples, medical instrument 1104 may not be visible in the virtual image.

In some embodiments, display system 1110 may display a virtual navigational image in which the actual location of medical instrument 1104 is registered with preoperative or concurrent images to present the operator O with a virtual image of medical instrument 1104 within the surgical site from an external viewpoint. An image of a portion of medical instrument 1104 or other graphical or alphanumeric indicators may be superimposed on the virtual image to assist operator O in the control of medical instrument 1104. As described herein, visual representations of data points may be rendered to display system 1110. For example, measured data points, moved data points, registered data points, and other data points described herein may be displayed on display system 1110 in a visual representation. The data points may be visually represented in a user interface by a plurality of points or dots on display system 1110 or as a rendered model, such as a mesh or wire model created based on the set of data points. In some examples, the data points may be color coded according to the data they represent. In some embodiments, a visual representation may be refreshed in display system 1110 after each processing operation has been implemented to alter data points.

Teleoperated medical system 1100 may also include control system 1112. Control system 1112 includes at least one memory and at least one computer processor (not shown) for effecting control between medical instrument 1104, master assembly 1106, sensor system 1108, and display system 1110. Control system 1112 also includes programmed instructions (e.g., a non-transitory machine-readable medium storing the instructions) to implement some or all of the methods described in accordance with aspects disclosed herein, including instructions for providing information to display system 1110. While control system 1112 is shown as a single block in the simplified schematic of FIG. 11, the system may include two or more data processing circuits with one portion of the processing optionally being performed on or adjacent to manipulator assembly 1102, another portion of the processing being performed at master assembly 1106, and/or the like. The processors of control system 1112 may execute instructions comprising instruction corresponding to processes disclosed herein, such as controlling the dynamically adjusting antenna parameters according embodiments discussed above. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 1112 supports wireless communication protocols such as Bluetooth, IrDA, HomeRF, IEEE 802.11, DECT, and Wireless Telemetry.

In some embodiments, control system 1112 may receive force and/or torque feedback from medical instrument 1104. Responsive to the feedback, control system 1112 may transmit signals to master assembly 1106. In some examples, control system 1112 may transmit signals instructing one or more actuators of manipulator assembly 1102 to move medical instrument 1104. Medical instrument 1104 may extend into an internal surgical site within the body of patient P via openings in the body of patient P. Any suitable conventional and/or specialized actuators may be used. In some examples, the one or more actuators may be separate from, or integrated with, manipulator assembly 1102. In some embodiments, the one or more actuators and manipulator assembly 1102 are provided as part of a teleoperational cart positioned adjacent to patient P and operating table T.

Control system 1112 may optionally further include a virtual visualization system to provide navigation assistance to operator O when controlling medical instrument 1104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 1108 may be used to compute an approximate location of medical instrument 1104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 1100 may further include optional operations and support systems (not shown) such as illumination systems, steering control systems, irrigation systems, and/or suction systems. In some embodiments, teleoperated medical system 1100 may include more than one manipulator assembly and/or more than one master assembly. The exact number of teleoperational manipulator assemblies will depend on the surgical procedure and the space constraints within the operating room, among other factors. Master assembly 1106 may be collocated or they may be positioned in separate locations. Multiple master assemblies allow more than one operator to control one or more teleoperational manipulator assemblies in various combinations.

Figure 12A:
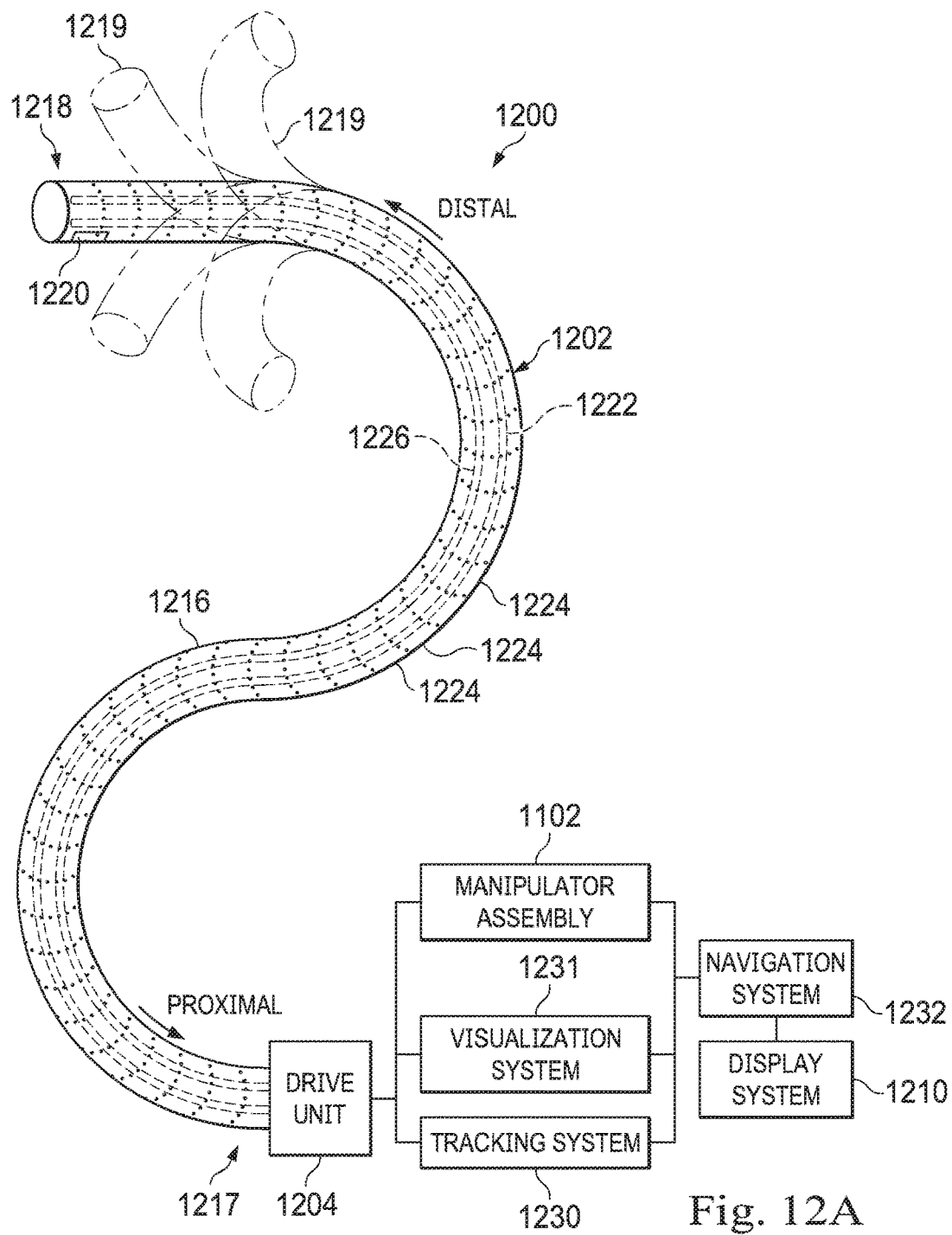
FIG. 12A is a simplified diagram of a medical instrument system according to some embodiments.

FIG. 12A is a simplified diagram of a medical instrument system 1200 according to some embodiments. In some embodiments, medical instrument system 1200 may be used as medical instrument 1104 in an image-guided medical procedure performed with teleoperated medical system 1100. In some examples, medical instrument system 1200 may be used for non-teleoperational exploratory procedures or in procedures involving traditional manually operated medical instruments, such as endoscopy as well as RF tissue ablation. Optionally medical instrument system 1200 may be used to gather (i.e., measure) a set of data points corresponding to locations within anatomic passageways of a patient, such as patient P.

Medical instrument system 1200 includes elongate device 1202, such as a flexible catheter, coupled to a drive unit 1204. Elongate device 1202 includes a flexible body 1216 having proximal end 1217 and distal end or tip portion 1218. In some embodiments, flexible body 1216 has an approximately 3 mm outer diameter. Other flexible body outer diameters may be larger or smaller.

Medical instrument system 1200 further includes a tracking system 1230 for determining the position, orientation, speed, velocity, pose, and/or shape of distal end 1218 and/or of one or more segments 1224 along flexible body 1216 using one or more sensors and/or imaging devices as described in further detail below. The entire length of flexible body 1216, between distal end 1218 and proximal end 1217, may be effectively divided into segments 1224. Tracking system 1230 may optionally be implemented as hardware, firmware, software or a combination thereof which interact with or are otherwise executed by one or more computer processors, which may include the processors of control system 1112 in FIG. 11.

Tracking system 1230 may optionally track distal end 1218 and/or one or more of the segments 1224 using a shape sensor 1222. Shape sensor 1222 may optionally include an optical fiber aligned with flexible body 1216 (e.g., provided within an interior channel (not shown) or mounted externally). In one embodiment, the optical fiber has a diameter of approximately 200 μm. In other embodiments, the dimensions may be larger or smaller. The optical fiber of shape sensor 1222 forms a fiber optic bend sensor for determining the shape of flexible body 1216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 1216 can be used to reconstruct the shape of flexible body 1216 over the interval of time. In some embodiments, tracking system 1230 may optionally and/or additionally track distal end 1218 using a position sensor system 1220. Position sensor system 1220 may be a component of an EM sensor system with position sensor system 1220 including one or more conductive coils that may be subjected to an externally generated electromagnetic field. Each coil of the EM sensor system then produces an induced electrical signal having characteristics that depend on the position and orientation of the coil relative to the externally generated electromagnetic field. In some embodiments, position sensor system 1220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 1230 may alternately and/or additionally rely on historical pose, position, or orientation data stored for a known point of an instrument system along a cycle of alternating motion, such as breathing. This stored data may be used to develop shape information about flexible body 1216. In some examples, a series of positional sensors (not shown), such as electromagnetic (EM) sensors similar to the sensors in position sensor 1220 may be positioned along flexible body 1216 and then used for shape sensing, in some embodiments with sufficient distance from the medical instrument 1104 (e.g., a flexible antenna system 100 according to embodiments). In some examples, a history of data from one or more of these sensors taken during a procedure may be used to represent the shape of elongate device 1202, particularly if an anatomic passageway is generally static.

Figure 12B:
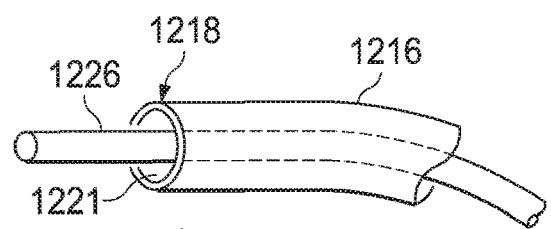
FIG. 12B is a simplified diagram of a medical instrument with an extended medical tool according to some embodiments.

Flexible body 1216 includes a channel 1221 sized and shaped to receive a medical instrument 1226. FIG. 12B is a simplified diagram of flexible body 1216 with medical instrument 1226, such as an ablation tool (such as microwave ablation) extended according to some embodiments. In some embodiments, medical instrument 1226 may be used for procedures such as surgery, biopsy, ablation, illumination, irrigation, or suction. Medical instrument 1226 can be deployed through channel 1221 of flexible body 1216 and used at a target location within the anatomy. Medical instrument 1226 may include, for example, image capture probes, biopsy instruments, laser ablation fibers, and/or other surgical, diagnostic, or therapeutic tools. Medical tools may include, in addition to ablation antennae such as the flexible antenna system 100, end effectors having a single working member such as a scalpel, a blunt blade, an optical fiber, an electrode, and/or the like. Medical instrument 1226 may also be used with an image capture probe also within flexible body 1216. In various embodiments, medical instrument 1226 may be an image capture probe that includes a distal portion with a stereoscopic or monoscopic camera at or near distal end 1218 of flexible body 1216 for capturing images (including video images) that are processed by a visualization system 1231 for display and/or provided to tracking system 1230 to support tracking of distal end 1218 and/or one or more of the segments 1224. The image capture probe may include a cable coupled to the camera for transmitting the captured image data. In some examples, the image capture instrument may be a fiber-optic bundle, such as a fiberscope, that couples to visualization system 1231. The image capture instrument may be single or multi-spectral, for example capturing image data in one or more of the visible, infrared, and/or ultraviolet spectrums. Alternatively, medical instrument 1226 may itself be the image capture probe. Medical instrument 1226 may be advanced from the opening of channel 1221 to perform the procedure and then retracted back into the channel when the procedure is complete. Medical instrument 1226 may be removed from proximal end 1217 of flexible body 1216 or from another optional instrument port (not shown) along flexible body 1216.

Medical instrument 1226 may additionally house cables, linkages, or other actuation controls (not shown) that extend between its proximal and distal ends to controllably bend the distal end of medical instrument 1226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 1216 may also house cables, linkages, or other steering controls (not shown) that extend between drive unit 1204 and distal end 1218 to controllably bend distal end 1218 as shown, for example, by broken dashed line depictions 1219 of distal end 1218. In some examples, at least four cables are used to provide independent "up-down" steering to control a pitch of distal end 1218 and "left-right" steering to control a yaw of distal end 1281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 1200 is actuated by a teleoperational assembly, drive unit 1204 may include drive inputs that removably couple to and receive power from drive elements, such as actuators, of the teleoperational assembly. In some embodiments, medical instrument system 1200 may include gripping features, manual actuators, or other components for manually controlling the motion of medical instrument system 1200. Elongate device 1202 may be steerable or, alternatively, the system may be non-steerable with no integrated mechanism for operator control of the bending of distal end 1218. In some examples, one or more lumens, through which medical instruments can be deployed and used at a target surgical location, are defined in the walls of flexible body 1216.

In some embodiments, medical instrument system 1200 may include a flexible bronchial instrument, such as a bronchoscope or bronchial catheter, for use in examination, diagnosis, biopsy, or treatment of a lung. Medical instrument system 1200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like. Medical instrument system 1200 may provide a working lumen to delivery tools such as diagnostic devices and/or or treatment tools including biopsy needles, ablation tools including antenna systems such as flexible antenna system 100, and/or the like. Alternatively, medical instrument system 1200 may include integrated biopsy and/or treatment tools including an integrated antenna system such as flexible antenna system 100.

The information from tracking system 1230 may be sent to a navigation system 1232 where it is combined with information from visualization system 1231 and/or the preoperatively obtained models to provide the physician or other operator with real-time position information. In some examples, the real-time position information may be displayed on display system 1110 of FIG. 11 for use in the control of medical instrument system 1200. In some examples, control system 1112 of FIG. 11 may utilize the position information as feedback for positioning medical instrument system 1200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 1200 may be teleoperated within medical system 1100 of FIG. 11. In some embodiments, manipulator assembly 1102 of FIG. 11 may be replaced by direct operator control. In some examples, the direct operator control may include various handles and operator interfaces for hand-held operation of the instrument.

Figure 13A:
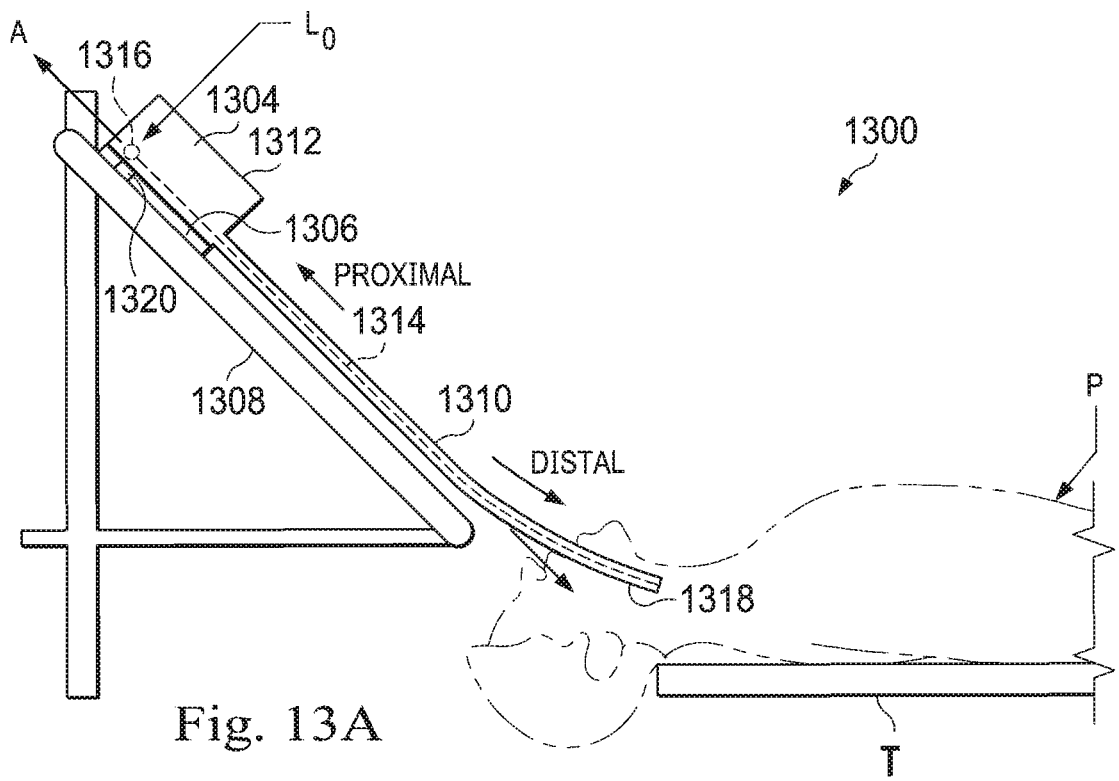
FIGS. 13A and 13B are simplified diagrams of side views of a patient coordinate space including a medical instrument mounted on an insertion assembly according to some embodiments.
Figure 13B:
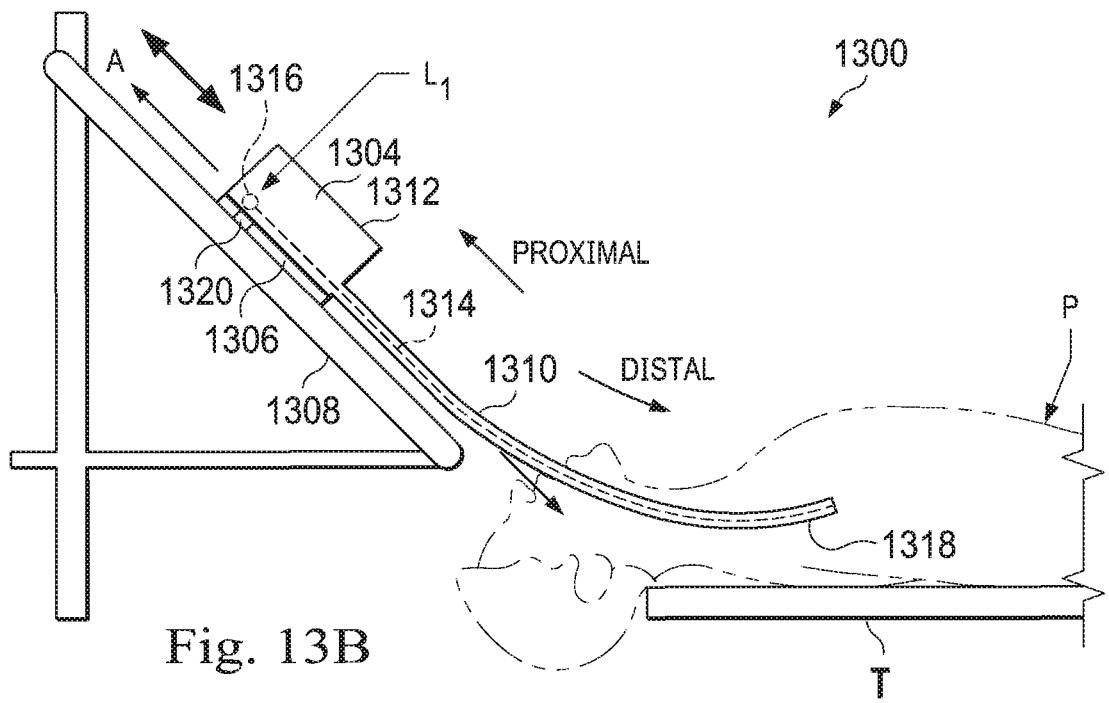

FIGS. 13A and 13B are simplified diagrams of side views of a patient coordinate space including a medical instrument mounted on an insertion assembly according to some embodiments. As shown in FIGS. 13A and 13B, a surgical environment 1300 includes a patient P is positioned on the table T of FIG. 11. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific phase in respiration, and tagged and identified with that phase. In some embodiments, the phase during which data is collected may be inferred from physiological information collected from patient P. Within surgical environment 1300, a point gathering instrument 1304 is coupled to an instrument carriage 1306. In some embodiments, point gathering instrument 1304 may use EM sensors, shape-sensors, and/or other sensor modalities. Instrument carriage 1306 is mounted to an insertion stage 1308 fixed within surgical environment 1300. Alternatively, insertion stage 1308 may be movable but have a known location (e.g., via a tracking sensor or other tracking device) within surgical environment 1300. Instrument carriage 1306 may be a component of a manipulator assembly (e.g., manipulator assembly 1102) that couples to point gathering instrument 1304 to control insertion motion (i.e., motion along the A axis) and, optionally, motion of a distal end 1318 of an elongate device 1310 in multiple directions including yaw, pitch, and roll. Instrument carriage 1306 or insertion stage 1308 may include actuators, such as servomotors, (not shown) that control motion of instrument carriage 1306 along insertion stage 1308.

Elongate device 1310 is coupled to an instrument body 1312. Instrument body 1312 is coupled and fixed relative to instrument carriage 1306. In some embodiments, an optical fiber shape sensor 1314 is fixed at a proximal point 1316 on instrument body 1312. In some embodiments, proximal point 1316 of optical fiber shape sensor 1314 may be movable along with instrument body 1312 but the location of proximal point 1316 may be known (e.g., via a tracking sensor or other tracking device). Shape sensor 1314 measures a shape from proximal point 1316 to another point such as distal end 1318 of elongate device 1310. Point gathering instrument 1304 may be substantially similar to medical instrument system 1200.

A position measuring device 1320 provides information about the position of instrument body 1312 as it moves on insertion stage 1308 along an insertion axis A. Position measuring device 1320 may include resolvers, encoders, potentiometers, and/or other sensors that determine the rotation and/or orientation of the actuators controlling the motion of instrument carriage 1306 and consequently the motion of instrument body 1312. In some embodiments, insertion stage 1308 is linear. In some embodiments, insertion stage 1308 may be curved or have a combination of curved and linear sections.

FIG. 13A shows instrument body 1312 and instrument carriage 1306 in a retracted position along insertion stage 1308. In this retracted position, proximal point 1316 is at a position $L_0$ on axis A. In this position along insertion stage 1308 an A component of the location of proximal point 1316 may be set to a zero and/or another reference value to provide a base reference to describe the position of instrument carriage 1306, and thus proximal point 1316, on insertion stage 1308. With this retracted position of instrument body 1312 and instrument carriage 1306, distal end 1318 of elongate device 1310 may be positioned just inside an entry orifice of patient P. Also in this position, position measuring device 1320 may be set to a zero and/or another reference value (e.g., I=0). In FIG. 13B, instrument body 1312 and instrument carriage 1306 have advanced along the linear track of insertion stage 1308 and distal end 1318 of elongate device 1310 has advanced into patient P. In this advanced position, the proximal point 1316 is at a position $L_1$ on the axis A. In some examples, encoder and/or other position data from one or more actuators controlling movement of instrument carriage 1306 along insertion stage 1308 and/or one or more position sensors associated with instrument carriage 1306 and/or insertion stage 1308 is used to determine the position $L_x$ of proximal point 1316 relative to position $L_0$. In some examples, position $L_x$ may further be used as an indicator of the distance or insertion depth to which distal end 1318 of elongate device 1310 is inserted into the passageways of the anatomy of patient P.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A flexible instrument, comprising:
    an antenna having a distal tip portion shaped to perforate tissue of a patient, a proximal base, and an antenna body therebetween, wherein the antenna body comprises a patterned cylindrical structure having antenna body elements that are spatially separated from each other, the antenna body having a proximal end coupled to the proximal base and a distal end coupled to the distal tip portion, wherein the distal tip portion is disposed distally of the distal end of the antenna body, the antenna comprising:
        a first material having a flexible plastic deformation limit allowing recovery of the antenna body to a substantially initial state after being formed into a tight bend; and
        a second material plated onto the first material, wherein the second material being more conductive than the first material; and
    an adjustment device configured to adjust pitch lengths between adjacent antenna body elements, wherein the flexible instrument is configured to generate a radiation pattern from the antenna that varies based on the pitch lengths between the adjacent antenna body elements to ablate tissue.

2. The flexible instrument of claim 1, wherein the tight bend has a bend radius of less than approximately 30 mm.

3. The flexible instrument of claim 1, wherein the first material comprises at least one of stainless steel, nickel titanium, and beryllium copper, and the second material comprises at least one of gold and silver.

4. The flexible instrument of claim 1, further comprising a conducting cable assembly comprising an inner conductor and an outer conductor wherein the antenna and the conducting cable assembly are coupled.

5. The flexible instrument of claim 4, wherein the proximal base couples to the outer conductor of the conducting cable assembly.

6. The flexible instrument of claim 4, further comprising a spacer, wherein the proximal base of the antenna couples to the spacer near the outer conductor of the conducting cable assembly.

7. The flexible instrument of claim 1, further comprising a conducting cable including an inner conductor and an outer conductor, wherein the antenna is integrally formed as part of the outer conductor of the conducting cable.

8. The flexible instrument of claim 7, wherein the antenna body of the antenna is coupled to the inner conductor of the conducting cable.

9. The flexible instrument of claim 8, wherein the proximal base of the antenna is in abutment with the inner conductor.

10. The flexible instrument of claim 8, wherein a lumen extends through the patterned cylindrical structure and the inner conductor extends into the lumen and is coupled to the antenna body.

11. The flexible instrument of claim 8, wherein a lumen extends through the patterned cylindrical structure and the inner conductor extends through the lumen and couples to the distal tip portion.

12. The flexible instrument of claim 1, wherein the antenna body comprises a material with a double bar ring configuration cut from the material, a single bar ring configuration cut from the material, or a helical coil cut from the material.

13. The flexible instrument of claim 1, wherein the distal tip portion comprises at least one of a plastic and a metal.

14. The flexible instrument of claim 1, wherein the distal tip portion is integral with the antenna body.

15. The flexible instrument of claim 1, wherein the distal tip portion is formed from at least two different materials.

16. The flexible instrument of claim 1, wherein the antenna body comprises a material with a non-symmetrical pattern formed from slots cut from the material.

17. The flexible instrument of claim 1, wherein the adjustment device comprises a push/pull element.

18. The flexible instrument of claim 4, wherein the adjustment device comprises a sheath configured to slide relative to the conducting cable assembly.

19. The flexible instrument of claim 1, wherein the flexible instrument is in operative communication with a control system configured to shift an operating frequency of power applied to the antenna to adjust for a change of a center frequency of operation of the antenna caused by adjusting the pitch lengths between the adjacent antenna body elements.

* * * * *